US008108030B2

(12) United States Patent
Castella et al.

(10) Patent No.: US 8,108,030 B2
(45) Date of Patent: Jan. 31, 2012

(54) METHOD AND APPARATUS TO IDENTIFY VULNERABLE PLAQUES WITH THERMAL WAVE IMAGING OF HEATED NANOPARTICLES

(75) Inventors: Paul Castella, San Antonio, TX (US); Jihoon Kim, Evanston, IL (US)

(73) Assignees: Board of Regents, The University of Texas System, Austin, TX (US); Volcano Corporation, San Diego, CA (US)

( * ) Notice: Subject to any disclaimer, the term of this patent is extended or adjusted under 35 U.S.C. 154(b) by 88 days.

(21) Appl. No.: 11/876,643

(22) Filed: Oct. 22, 2007

(65) Prior Publication Data

US 2008/0095714 A1    Apr. 24, 2008

Related U.S. Application Data

(63) Continuation-in-part of application No. 11/784,477, filed on Apr. 6, 2007, now Pat. No. 7,801,590.

(60) Provisional application No. 60/862,429, filed on Oct. 20, 2006.

(51) Int. Cl.
*A61B 6/00* (2006.01)
(52) U.S. Cl. .................................................. 600/474
(58) Field of Classification Search .............. 600/474, 600/407; 607/98
See application file for complete search history.

(56) References Cited

U.S. PATENT DOCUMENTS

| 4,676,980 | A | 6/1987 | Segal et al. ..................... 424/85 |
| 4,816,567 | A | 3/1989 | Cabilly et al. ................. 530/387 |
| 5,565,332 | A | 10/1996 | Hoogenboom et al. ..... 435/69.1 |
| 5,596,079 | A | 1/1997 | Smith et al. ................... 530/328 |
| 5,824,520 | A | 10/1998 | Mulligan-Kehoe ........ 435/91.41 |
| 6,031,071 | A | 2/2000 | Mandeville et al. .......... 530/300 |
| 6,290,668 | B1 | 9/2001 | Gregory et al. ................. 604/22 |
| 6,530,944 | B2 * | 3/2003 | West et al. ...................... 607/88 |
| 6,756,591 | B1 * | 6/2004 | Lounis et al. ............. 250/316.1 |
| 6,997,863 | B2 * | 2/2006 | Handy et al. ...................... 600/9 |
| 2005/0075704 | A1 | 4/2005 | Tu et al. ......................... 607/88 |
| 2005/0090732 | A1 | 4/2005 | Ivkov et al. ................... 600/411 |
| 2005/0149152 | A1 | 7/2005 | Bertolero et al. .............. 607/96 |
| 2005/0171433 | A1 * | 8/2005 | Boppart et al. ............... 600/473 |
| 2005/0175540 | A1 | 8/2005 | Oraevsky et al. ............ 424/9.5 |
| 2007/0038121 | A1 | 2/2007 | Feldman et al. ............. 600/476 |
| 2007/0208400 | A1 * | 9/2007 | Nadkarni et al. ............ 607/100 |
| 2007/0224169 | A1 * | 9/2007 | Sliwa et al. ................. 424/93.2 |

FOREIGN PATENT DOCUMENTS

| WO | 93/06213 | 4/1993 |
| WO | 93/08829 | 5/1993 |
| WO | 2004/096049 | 11/2004 |

OTHER PUBLICATIONS

Telenkov et al, Coherent Thermal wave Imaging of Subsurface Chromophores in Biological Materials, Feb. 1, 2002, Physics in Medicine and Biology, 47 (2002), 657-671.*

Anderson et al., Selective photothermolysis: Precise microsurgery by selective absorption of pulsed radiation, Science, 220 (4596):524-527 (1983).

(Continued)

*Primary Examiner* — Jacqueline Cheng
(74) *Attorney, Agent, or Firm* — J. Peter Paredes; Rosenbaum & Silvert, P.C.

(57) ABSTRACT

Provided herein are systems, methods, and compositions for the thermal imaging of cells with nanoparticles.

20 Claims, 11 Drawing Sheets

OTHER PUBLICATIONS

Bonnemain, Superparamagnetic agents in magnetic resonance imaging: physicochemical characteristics and clinical applications. A review., J Drug Target, 6(3):167-74 (1998) Abstract.

Cavaleri et al., Femtosecond study of the size-dependent charge carrier dynamics in ZnO nanocluster solutions J Chem Phys, 103(13):5378 (1995).

Cherepy et al., Ultrafast studies of photoexcited electron dynamics in $\gamma$- and $\alpha$-$Fe_2O_3$ semiconductor nanoparticles, J Phys Chem. B, 102: 770-776 (1998).

Clackson et al., Making antibody fragments using phage display libraries, Nature, 352:624-628 (1991).

Colombo et al., Femtosecond study of the intensity dependence of electron-hole dynamics in $TiO_2$ nanoclusters, Chemical Physics Letters, 232: 207-214 (1995).

David et al., Protein iodination with solid state lactoperoxidase, Biochemistry, 13(5):1014-1021 (1974).

Elghanian et al., Selective colorimetric detection of polynucleotides based on the distance-dependent optical properties of gold nanoparticles, Science, 277(5329):1078-1081 (1997).

Griffiths et al., Human anti-self antibodies with high specificity from phage display libraries, The EMBO Journal, 12(2):725-734 (1993).

Griffiths et al., Isolation of high affinity human antibodies directly from large synthetic repertoires, The EMBO Journal, 13(14):3245-3260 (1994).

Hawes et al., Spectrally selective heating of nanosized particles by surface plasmon resonance, Journal of Quantitative Spectroscopy & Radiative Transfer 104: 199-207 (2007).

Hunter et al., Preparation of iodine-131 labelled human growth hormone of high specific activity, Nature, 194(4827):495-496 (1962).

Jakobovits et al., Germ-line transmission and expression of a human-derived yeast artificial chromosome, Nature, 362:255-258 (1993).

Jakobovits et al., Analysis of homozygous mutant chimeric mice: Deletion of the immunoglobulin heavy-chain joining region blocks B-cell development and antibody production, PNAS, 90:2551-2555 (1993).

Johnson et al., Human antibody engineering, Current Opinion in Structural Biology, 3:564-571 (1993).

Jones et al., Replacing the complementarity-determining regions in a human antibody with those from a mouse, Nature, 321:522-525 (1986).

Jung et al., Physical and chemical properties of superparamagnetic iron oxide MR contrast agents: Ferumoxides, ferumoxtran, ferumoxsil, Magnetic Resonance Imaging, 13(5): 661-674 (1995).

Kelly et al., Detection of Vascular Adhesion Molecule-1 expression using a novel multimodal nanoparticle, Circulation Research, 96:327-336 (2005).

Kim, Measurement of Optical Path Length Change in response to Pulsed Laser Irradiation Using Phase Sensitive OCT, Dissertation Presented to the Faculty of the Graduate School of the University of Texas at Austin in Partial Fulfillment of the Requirements for the Degree of Doctoral of Philosophy, The University of Texas at Austin (2006).

Kohler et al., Continuous cultures of fused cells secreting antibody of predefined specificity, Nature, 256:495-497 (1975).

Kozbor et al., A human hybrid myeloma for production of human monoclonal antibodies, The Journal of Immunology. 133(6):3001-3005 (1984).

Litovsky et al., Superparamagnetic iron oxide—based method for quantifying recruitment of monocytes to mouse atherosclerotic lesions in vivo: Enhancement by Tissue Necrosis Factor-$\alpha$, Interleukin-1$\beta$, and Interferon-$\gamma$, Circulation, 107:1545-1549 (2003).

Loo et al., Nanoshell-enabled photonics-based imaging and therapy of cancer, Technology in Cancer Research & Treatment, 3(1): 33-40 (2004).

Marks et al., By-passing Immunization: Human antibodies from V-gene libraries displayed on phage, J Mol Biol. 222:581-597 (1991).

Marks et al., By-passing immunization: Building high affinity human antibodies by chain shuffling, Nature Biotechnology, 10:779-783 (1992).

McCafferty et al., Phage antibodies: Filamentous phage displaying antibody variable domains, Nature, 348:552-554 (1990).

Milstein et al., Hybrid hybridomas and their use in immunohistochemistry, Nature, 305:537-540 (1983).

Moreno et al., Macrophage infiltration in acute coronary syndromes. Implications for plaque rupture, Circulation, 90:775-778 (1994).

Morrison et al., Chimeric human antibody molecules: Mouse antigen-binding domains with human constant region domains, PNAS. 81(21):6851-6855 (1984).

Munson et al., Ligand: A versatile computerized approach for characterization of ligand-binding systems, Analytical Biochemistry, 107:220-239 (1980).

Nygren, Conjugation of horseradish peroxidase to Fab fragments with different homobifunctional and heterobifunctional cross-linking reagents. A comparative study, The Journal of Histochemistry and Cytochemistry, 30(5):407-412 (1982).

Oldenburg et al., Nanoengineering of optical resonances, Chemical Physics Letters, 288:243-247 (1998).

Pain et al., Preparation of protein A-peroxidase monoconjugate using a heterobifunctional reagent, and its use in enzyme immunoassays, Journal of Immunological Methods, 40:219-230 (1981).

Pitsillides et al., Selective cell targeting with light-absorbing microparticles and nanoparticles, Biophysical Journal, 84: 4023-4032 (2003).

Pulido et al., Imaging of atherosclerotic plaque, Int J Cardiovasc Imaging, 20(6):553-9 (2004) Abstract.

Riechmann et al., Reshaping human antibodies for therapy, Nature, 332:323-327 (1988).

Rogers et al., Factors regulating macrophage endocytosis of nanoparticles: implications for targeted magnetic resonance plaque imaging Atherosclerosis, 178: 67-73 (2005).

Ruehm et al., Magnetic resonance imaging of atherosclerotic plaque with ultrasmall superparamagnetic particles of iron oxide in hyperlipidemic rabbits, Circulation, 103:415-422 (2001).

Schmermund et al., Intracoronary thermography, Herz, 28:505-512 (2003).

Schmitz et al., Superparamagnetic iron oxide—enhanced MRI of atherosclerotic plaques in Watanabe hereditable hyperlipidemic rabbits, Investigative Radiology, 35(8): 460-471 (2000).

Stefanadis et al., Thermal heterogeneity within human atherosclerotic coronary arteries detected in vivo: A new method of detection by application of a special thermography catheter, Circulation, 99:1965-1971 (1999).

Suresh et al., Bispecific monoclonal antibodies from hybrid hybridomas, Methods in Enzymology, 121:210-228 (1986).

Traunecker et al., Bispecific single chain molecules (Janusins) target cytotoxic lymphocytes on HIV infected cells, The EMBO Journal, 10(12):3655-3659 (1991).

Turro et al., Spectroscopic probe of the surface of iron oxide nanocrystals, Nano Letters, 2(4): 325-328 (2002).

Tyagi, Homocysteine redox receptor and regulation of extracellular matrix components in vascular cells, Am J Physiol Cell Physiol, 274:396-405 (1998).

Verheye et al., In vivo temperature heterogeneity of atherosclerotic plaques is determined by plaque composition, Circulation, 105: 1596-1601 (2002).

Verhoeyen et al., Reshaping human antibodies: Grafting an antilysozyme activity, Science, 239(4847):1534-1536 (1988).

Waterhouse et al., Combinatorial infection and in vivo recombination: a strategy for making large phage antibody repertoires, Nucleic Acids Research, 21:2265-2266 (1993).

Weissleder et al., MR lymphography: Study of a high-efficiency lymphotrophic agent, Radiology, 191:225-230 (1994).

Zhang et al., Size quantization and interfacial effects on a novel $\gamma$-$Fe_2O_3$/$SiO_2$ magnetic nanocomposite via sol-gel matrix-mediated synthesis, J Appl Phys, 81 (10):6892-6900 (1997).

* cited by examiner

METHOD AND APPARATUS TO IDENTIFY VULNERABLE PLAQUES WITH THERMAL WAVE IMAGING OF HEATED NANOPARTICLES

CROSS-REFERENCE TO RELATED APPLICATIONS

The present application claims priority to U.S. Provisional Application, U.S. Ser. No. 60/862,429, filed Oct. 20, 2006 and is a continuation-in-part of U.S. Ser. No. 11/784,477, filed Apr. 6, 2007 now U.S. Pat. No. 7,801,590.

BACKGROUND OF THE INVENTION

The invention generally relates to thermal wave imaging, and more particularly relates to thermal wave imaging with nanoparticles.

Atherosclerosis is a common human ailment arising from the deposition of fatty-like substances, referred to as atheromas or plaques, on the walls of blood vessels. While some plaques are relatively stable, others are vulnerable to rupture and release their contents into the bloodstream, causing a blood clot to form. Heart attacks and other acute cardiovascular events usually result from the rupture of high-risk, vulnerable plaques in coronary arteries. Vulnerable plaques are believed to have three major characteristics—a deposit of lipids, a thin cap of fibrous material covering the lipid pool, and infiltration of the immune cells called macrophages. Such deposits occur in both the peripheral blood vessels, and the coronary vessels. When deposits accumulate in localized regions of a blood vessel, stenosis, or narrowing of the vascular channel occurs. Blood flow is restricted and the person's health is at serious risk. Early detection and characterization of arterial plaque can identify patients who are unaware that they are at risk of suffering a myocardial infarction or other cardiovascular events such as stroke.

Recently, temperature differences correlated positively with cell macrophage density in atherosclerotic plaques. Thermal heterogeneity is increased in unstable atherosclerotic plaques compared to stable plaques, roughly by 0.3° C. from macrophage activity and the inflammatory response thereof. However, recent mechanisms to determine the thermal changes in the plaques are complicated by the cooling effect of blood flow causing a high signal-to-noise ration in the thermal imaging techniques. Such complications do not result in precise location of unstable atherosclerotic plaques.

The present invention attempts to overcome the shortcomings of the cooling effect of blood flow by administering a plurality of metallic nanoparticles to localize in macrophages, heating such nanoparticles with a pulsed laser, and imaging the temperature affects in the plaque with a thermal sensor.

SUMMARY OF THE INVENTION

Provided herein are systems, methods and compositions for a method and apparatus to identify vulnerable plaques by thermal wave imaging of heated nanoparticles.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

The accompanying drawings, which are incorporated in and constitute a part of this specification, illustrate aspects of the methods, apparatuses, and systems and together with the description, serve to explain the principles of the methods, apparatuses, and systems.

DETAILED DESCRIPTION OF THE INVENTION

The methods, apparatuses, and systems can be understood more readily by reference to the following detailed description of the methods, apparatuses, and systems and the Examples included therein and to the Figures and their previous and following description.

Before the present compounds, compositions, articles, devices, and/or methods are disclosed and described, it is to be understood that these are not limited to specific synthetic methods, specific components, or to particular compositions, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a nanoparticle" includes mixtures of nanoparticles, reference to "a nanoparticle" includes mixtures of two or more such nanoparticles, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. For example, the phrase "optionally substituted shelled metals" means that shelled metals may or may not be substituted and that the description includes both unsubstituted shelled metals and shelled metals where there is substitution.

As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. In one aspect, the subject is a mammal such as a primate or a human, alternatively, cats, dogs, and other livestock may be used for testing purposes. The term does not denote a particular age or sex. Thus, adult and newborn subjects, as well as fetuses, whether male or female, are intended to be covered.

Reference will now be made in detail to exemplary aspects of the systems, methods, apparatuses, and/or compositions, examples of which are illustrated in the accompanying drawings.

Figure 1:
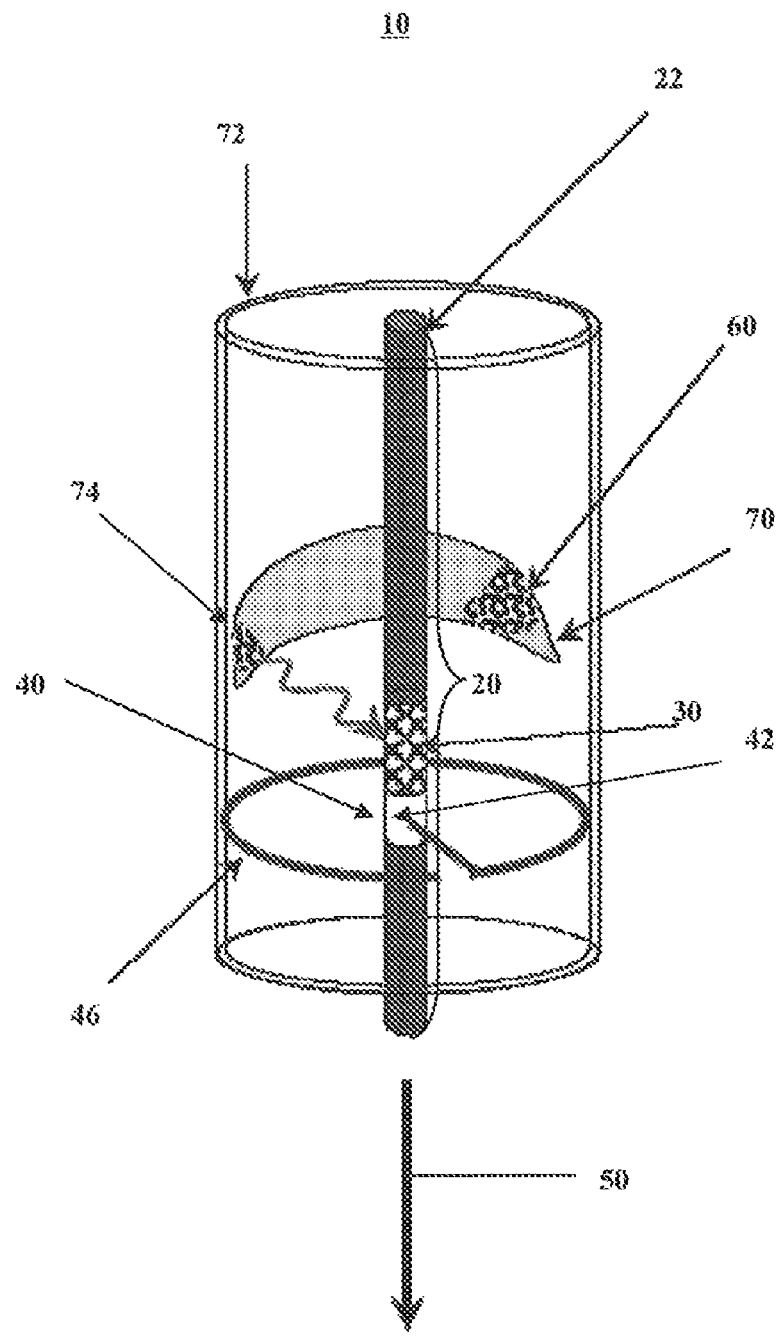
FIG. 1 is a schematic diagram of the thermal wave imaging system.
Figure 2A:
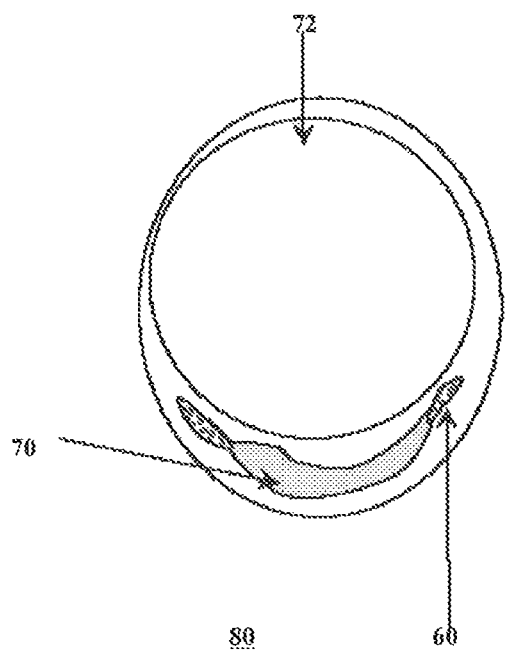
FIG. 2A is a cross-sectional view of a blood vessel with a plaque and localized nanoparticles imaged by the thermal wave imaging system.
Figure 2B:
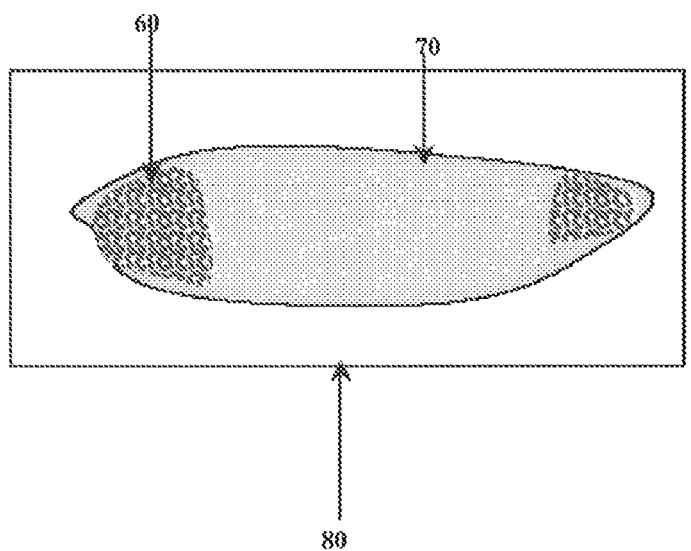
FIG. 2B is a cross sectional view of the plaque with localized nanoparticles.

As shown in FIG. 1, the thermal imaging apparatus 10 generally comprises a thermal sensor 30, a laser-heating element 40 coupled to the thermal sensor 30; a reflecting element 42 coupled to the laser heating element 40; and a catheter 20 coupled to the thermal imaging apparatus 10. A computer processor is coupled to the catheter 20 to produce a thermal image 80, as shown in FIGS. 2A and 2B. The thermal imaging apparatus 10 is coupled with nanoparticles 60 by the laser heating element 40 in order measure the increase of the temperature of plaques 70 due to inflammation in a blood vessel 72. Atherosclerotic plaques have an increased endogenous temperature due to inflammatory processes and metabolic congestion, i.e. increase density of macrophages 74. Macrophages selectively uptake nanoparticles 60, such as when they are administered into the bloodstream, and therefore the nanoparticles 60 will selectively accumulate at the site of macrophage concentration, such as in atherosclerotic plaques. Therefore, the temperature differences in the plaques 70 can be artificially increased by the nanoparticles selectively heated by a laser heating element 40, and thus an enhanced thermal image of the macrophages 74 can be produced.

In another embodiment of the invention, the thermal imaging apparatus 10 further comprises an optical coherence tomography system coupled to the thermal imaging apparatus 10. Alternatively, the thermal imaging apparatus 10 comprises an ultrasound system coupled to the thermal imaging apparatus 10. The thermal imaging apparatus 10 further allows for therapies based on the identification and location of macrophage-laden plaque, such as using the information to place stents (bare metal, drug eluting, covered). Additionally, treatments based on selective nanoparticle uptake could be administered, such as the method of heating to kill or inactivate the macrophage as described in provisional application Ser. No. 60/790,248. Alternatively, the light energy used to locate the nanoparticle bearing macrophages could be applied to selectively kill or inactivate or otherwise modify the activity of the macrophages, when coupled to a property of the nanoparticle, such as a particle bearing a light activated drug, pro-drug, or enzyme. In this example, the same apparatus could be used with a different frequency of light to provide specificity between the heating and treatment applications, or a treatment specific catheter could be employed subsequent to the identification method. The light-responsive treatment could also employ structural alterations of the nanoparticle 60 that provides for the release of a drug (or other agent) following the interaction of light (or resultant heating). A description of the nanoparticles 60 and their localization to macrophages 74 is described below.

Nanoparticles: Composition and Localization

As used herein the term nanoparticle includes any particle between 0.1 nm ("nanometers") and 1000.0 nm in size that reflects or scatters light at one wavelength while absorbing light at a different wavelength. An administered nanoparticle comprises a material with non-zero magnetic susceptibility. Nanoparticles can be selected so that they are sensitive to only a particular wavelength of light, so that different wavelengths of light can be used to identify and heat different-sized nanoparticles.

Nanoparticles may be solid, hollow or partially hollow and may be spherical or asymmetrical in shape. Optionally, the cross section of an asymmetric nanoparticle is oval or elliptical. As one of skill in the art will appreciate, however, other asymmetric shapes can be used. The nanoparticles can comprise shelled or multi-shelled nanoparticles. Shelled or multi-shelled nanoparticles may be have targeting ligands conjugated to the shell material wherein the targeting ligand has an affinity for or binds to a target site in a subject or ex vivo as described herein. Such shelled or multi-shelled nanoparticles can be made using techniques known in the art, for example, as described in Loo et al., "Nanoshell-Fnabled Photonics-Based Imaging and Therapy of Cancer," Tech. Cancer Res. and Treatment, (2004) 3(1) 33-40, which is incorporated herein by reference for the methods taught herein. Further, Oldenburg et al., "Nanoengineering of Optical Resonances," Chemical Physics Letters (1998) 288, 243-247, is incorporated herein by reference for methods of nanoshell synthesis.

One or more administered nanoparticle can localize to a desired target within the subject using passive or active targeting mechanisms. Passive targeting mechanisms take advantage of the subject's inherent defense mechanisms to highlight phagocytic cells naturally responsible for particle clearance. For example, macrophage rich areas are a pathological correlate to an unstable atherosclerotic plaque in a subject. Moreover, administered nanoparticles, for example, small superparamagnetic and ultrasmall superparamagnetic particles of iron oxide, are avidly taken up, or engulfed by, macrophages located in unstable plaques. Thus, through the subject's natural defense mechanism, wherein macrophages accumulate in an unstable atherosclerotic plaque and engulf administered nanoparticles, administered nanoparticles passively target the unstable plaque. Similarly, macrophages located in the eye of a subject may engulf nanoparticles. Such passive targeting of nanoparticles can be used with the methods and apparatuses described herein to highlight a plaque's instability or to highlight other accumulation of phagocytic cells.

Active targeting mechanisms generally refer to the use of ligand-directed, site-specific targeting of nanoparticles. A nanoparticle can be configured to localize to a desired target site in a subject using a wide variety of targeting ligands including, but not limited to, antibodies, polypeptides, peptides, nucleic acids, polysaccharides. Such nanoparticles are referred to herein as "targeted nanoparticles." Targeting ligands or fragments thereof may be used to target a nanoparticle to cellular, or other endogenous or exogenous biomarkers in the subject. Such a biomarkers or "target sites" may include, but are not limited to, proteins, polypeptides, peptides, polysaccharides, lipids, or antigenic portions thereof, which are expressed within the subject. When active targeting mechanisms are used to target a cell, the targeted nanoparticle is optionally internalized by the targeted cell.

Thus, using the disclosed methods, at least one administered nanoparticle can optionally localize within a macrophage located in the subject and/or at least one administered targeted nanoparticle can localize to a desired target site in the subject.

The methods and apparatuses are not, however, limited to in vivo administration to a subject. As would be clear to one skilled in the art, nanoparticles, including targeted nanoparticles, can be administered in vitro to an ex vivo sample with localization of the nanoparticle to a desired target site and subsequent imaging occurring in vitro. Moreover, a composition, including at least one nanoparticle can be administered to a subject in vivo, and a sample can be subsequently taken from the subject and imaged ex vivo using the methods and apparatuses described herein.

When using a targeted nanoparticle the target site in vivo or in vitro can be endogenous or exogenous. The target site can be selected from the group consisting of an organ, cell, cell type, blood vessel, thrombus, fibrin and infective agent. Optionally, the target site can be a neoplastic cell. The target site can also be an extracellular domain of a protein. Furthermore, the target site can be selected from the group consisting of a lung, bronchus, intestine, stomach, colon, heart, brain, blood vessel, cervix, bladder, urethra, skin, muscle, liver, kidney and blood. The target site can also be a cell. For example, a cell can be selected from the group consisting of, but not limited to, a neoplastic cell, a squameous cell, a transitional cell, a basal cell, a muscle cell, an epithelial cell, a lymphocyte, a leukocyte, an monocyte, a red blood cell, and a mucosal cell.

Thus, targeted nanoparticles can be targeted to a variety of cells, cell types, antigens (endogenous and exogenous), epitopes, cellular membrane proteins, organs, markers, tumor markers, angiogenesis markers, blood vessels, thrombus, fibrin, and infective agents. For example, targeted nanoparticles can be produced that localize to targets expressed in a subject. Optionally, the target is a protein, and may be a protein with an extracellular or transmembrane domain. Optionally, the target may be the extracellular domain of a protein.

Desired targets are generally based on, but not limited to, the molecular signature of various pathologies, organs and/or cells. For example, adhesion molecules such as integrin $\alpha v \beta 3$, intercellular adhesion molecule-1 (I-CAM-1), fibrinogen receptor GPIIb/IIIa and VEGF receptors are expressed in regions of angiogenesis, inflammation or thrombus. These molecular signatures can be used to localize nanoparticles through the use of a targeting ligand. The methods described herein optionally use nanoparticles targeted to VEGFR2, I-CAM-1, $\alpha v \beta 3$ integrin, $\alpha v$ integrin, fibrinogen receptor GPIIb/IIIa, P-selectin, and/or mucosal vascular adressin cell adhesion molecule-1.

As used in this invention, the term "epitope" is meant to include any determinant capable of specific interaction with a targeting ligand as described below. Epitopic determinants usually consist of chemically active surface groupings of molecules such as amino acids or sugar side chains and usually have specific three dimensional structural characteristics, as well as specific charge characteristics.

Targeting ligands specific for a molecule that is expressed or over-expressed in a cell, tissue, or organ targeted for imaging, such as pre-cancerous, cancerous, neoplastic, or hyperproliferative cells, tissues, or organs, may be used with the nanoparticles described herein. This use may include the in vivo or in vitro imaging, detection, or diagnosis of pre-cancerous, cancerous, neoplastic or hyperproliferative cells in a tissue or organ. The compositions and methods of the invention may be used or provided in diagnostic kits for use in detecting and diagnosing cancer.

As used herein, a targeted cancer to be imaged, detected or diagnosed can be selected from, but are not limited to, the group comprising lymphomas (Hodgkins and non-Hodgkins), B cell lymphoma, T cell lymphoma, myeloid leukemia, leukemias, mycosis fungoides, carcinomas, carcinomas of solid tissues, squamous cell carcinomas, adenocarcinomas, sarcomas, gliomas, blastomas, neuroblastomas, plasmacytomas, histiocytomas, melanomas, adenomas, hypoxic tumors, myelomas, AIDS-related lymphomas or sarcomas, metastatic cancers, bladder cancer, brain cancer, nervous system cancer, squamous cell carcinoma of head and neck, neuroblastoma/glioblastoma, ovarian cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, hematopoietic cancers, testicular cancer, colo-rectal cancers, prostatic cancer, or pancreatic cancer.

Pre-cancerous conditions to be imaged, detected or diagnosed include, but are not limited to, cervical and anal dysplasias, other dysplasias, severe dysplasias, hyperplasias, atypical hyperplasias, and neoplasias. As would be clear to one skilled in the art, however, additional cancers and pre-cancerous conditions can be imaged, detected or diagnosed using the methods and apparatuses described herein.

Using methods known in the art, and as described herein, targeting ligands, such as polyclonal or monoclonal antibodies, can be readily produced to desired target sites in a subject. Thus, a targeted nanoparticle can further comprise an antibody or a fragment thereof. Methods for preparing and characterizing antibodies are well known in the art (See, e.g., Antibodies: A Laboratory Manual, Cold Spring Harbor Laboratory, 1988; incorporated herein by reference for the methods taught therein).

Monoclonal antibodies may be obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the monoclonal antibodies of the invention may be made using the hybridoina method first described by Kohler & Milstein, Nature 256:495 (1975), or may be made by recombinant DNA methods (Cabilly, et al., U.S. Pat. No. 4,816,567).

In the hybridoma method, a mouse or other appropriate host animal, such as hamster is immunized to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

DNA encoding a monoclonal antibody may be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., Proc. Nat. Acad. Sci. 81, 6851 (1984), or by covalently joining to the immunoglobulin coding sequence all or part of the coding sequence for a non-immunoglobulin polypeptide. In that manner, "chimeric" or "hybrid" antibodies can be prepared that have the binding specificity of an anti-cancer, pre-cancer, or hyperproliferative cell or other target molecule as described herein. Optionally, the antibody used herein is "humanized" or fully human.

Non-immunoglobulin polypeptides can be substituted for the constant domains of an antibody of the invention, or they can be substituted for the variable domains of one antigen-combining site of an antibody of the invention to create a chimeric bivalent antibody comprising one antigen-combining site having specificity for a first antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

Methods for humanizing nonhuman antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature 321, 522-525 (1986); Riechmama et al., Nature 332, 323-327 (1988); Verhoeyen et al., Science 239, 1534-1536 (1988)), by substituting rodent CDRs or CDR sequences for the corresponding sequences of a human antibody. Accordingly, such "humanized" antibodies are chimeric antibodies, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Antibodies can be humanized with retention of high affinity for the target site antigen and other favorable biological properties. Humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target site antigen(s), is achieved. In general, the CDR residues are directly and most substantially involved in influencing antigen binding.

Human monoclonal antibodies can be made by a hybridoma method. Human myeloma and mouse-human heteromyeloma cell lines for the production of human monoclonal antibodies have been described, for example, by Kozbor, J. Immunol. 133, 3001 (1984), and Brodeur, et al., Monoclonal Antibody Production Techniques and Applications, pp. 51-63 (Marcel Delker, Inc., New York, 1987), herein incorporated by reference.

Transgenic animals (e.g., mice) can be used that are capable, upon immunization, of producing a repertoire of human antibodies in the absence of endogenous immunoglobulin production. For example, it has been described that the homozygous deletion of the antibody heavy chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., Proc. Natl. Acad. Sci. USA 90, 2551-255 (1993); Jakobovits et al., Nature 362, 255-258 (1993).

Alternatively, phage display technology (McCafferty et al., Nature 348, 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S, and Chiswell, David J., Current Opinion in Structural Biology 3, 564-571 (1993). Several sources of V-gene segments can be used for phage display. Clackson et al., Nature 352, 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222, 581-597 (1991), or Griffith et al., EMBO J. 12, 725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., Bio/Technol. 10, 779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires (also known as "the mother-of-all libraries") has been described by Waterhouse et al., Nucl. Acids Res. 21, 2265-2266 (1993), and the isolation of a high affinity human antibody directly from such large phage library is reported by Griffith et al., EMBO J. (1994), in press. Gene shuffling can also be used to derive human antibodies from rodent antibodies, where the human antibody has similar affinities and specificities to the starting rodent antibody. According to this method, which is also referred to as "epitope imprinting," the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published Apr. 1, 1993). Unlike traditional humanization of rodent antibodies by CDR grafting, this technique provides completely human antibodies, which have no framework or CDR residues of rodent origin.

Bispecific antibodies are monoclonal, preferably human or humanized, antibodies that have binding specificities for at least two different antigens. One of the binding specificities is for a first antigen and the other one is for a second antigen.

Traditionally, the recombinant production of bispecific antibodies is based on the coexpression of two immunoglobulin heavy chain-light chain pairs, where the two heavy chains have different specificities (Millstein and Cuello, Nature 305, 537-539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published May 13, 1993), and in Traunecker et al., EMBO 10, 3655-3659 (1991). For further details of generating bispecific antibodies see, for example, Suresh et al., Methods in Enzymology 121, 210 (1986), herein incorporated by reference.

Heteroconjugate antibodies are also within the scope of the described compositions and methods. Heteroconjugate antibodies are composed of two covalently joined antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

A variety of immunoassay formats may be used to select antibodies that selectively bind with a desired target site or target site antigen. For example, solid-phase ELISA immunoassays are routinely used to select antibodies selectively immunoreactive with a protein, protein variant, or fragment thereof. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem., 107:220 (1980).

Not only can a targeted nanoparticle comprise an antibody or fragment thereof, but a targeted nanoparticle can also comprise targeting ligand that is a polypeptide or a fragment thereof. Optionally, polypeptides that are internalized by target cells can be attached to the surface of a nanoparticle. Ligands that are internalized can optionally be used for internalization of a nanoparticle into a target cell. A modified phage library can be use to screen for specific polypeptide sequences that are internalized by desired target cells. For example, using the methods described in Kelly et al., "Detection of Vascular Adhesion Molecule-1 Expression Using a Novel Multimodal Nanoparticle," Circulation Res., (2005) 96:327-336, which is incorporated herein for the methods taught therein, polypeptides can be selected that are internalized by VCAM-1 expressing cells or other cells expressing a ligand of interest.

There are a number of methods for isolating proteins which can bind a desired target. For example, phage display libraries have been used to isolate numerous polypeptides that interact with a specific target. (See for example, U.S. Pat. Nos. 6,031,071; 5,824,520; 5,596,079; and 5,565,332 which are herein incorporated by reference at least for their material related to phage display and methods related to combinatorial chemistry). Thus targeted nanoparticles can comprise a polypeptide or fragments thereof that interact with a desired target. A targeted nanoparticle can also comprise a binding domain of an antibody or phage.

The term "polypeptide" or "peptide" is used broadly herein to mean two or more amino acids linked by a peptide bond. The term "fragment" or "proteolytic fragment" also is used herein to refer to a product that can be produced by a proteolytic reaction on a polypeptide, i.e., a peptide produced upon cleavage of a peptide bond in the polypeptide. A fragment can be produced by a proteolytic reaction, but it should be recognized that a fragment need not necessarily be produced by a proteolytic reaction but can be produced using methods of chemical synthesis or methods of recombinant DNA technology, to produce a synthetic peptide that is equivalent to a proteolytic fragment. It should be recognized that the term "polypeptide" is not used herein to suggest a particular size or number of amino acids comprising the molecule, and that a polypeptide of the invention can contain up to several amino acid residues or more.

A nanoparticle can bind selectively or specifically to a desired target site, and/or can be internalized by a target cell. Such selective or specific binding and/or internalization can be readily determined using the methods, systems and apparatuses described herein. For example, selective or specific binding can be determined in vivo or in vitro by administering a targeted nanoparticle and detecting an increase in light scattering from the nanoparticle bound to a desired target site or internalized into the desired target cell. Detection of light scattering can be measured using the systems and apparatuses described below.

Thus, a targeted nanoparticle can be compared to a control nanoparticle having all the components of the targeted nanoparticle except the targeting characteristics, such as a targeting ligand. By detecting increased light scattering from the targeted nanoparticle bound to a desired target site versus a control nanoparticle, the specificity or selectivity of binding or internalization can be determined. If an antibody, polypeptide, or fragment thereof, or other targeting ligand is used, as described throughout, selective or specific binding to a target can be determined based on standard antigen/polypeptide/epitope/antibody complementary binding relationships. Further, other controls can be used. For example, the specific or selective targeting of the nanoparticles can be determined by exposing targeted nanoparticles to a control tissue, which includes all the components of the test or subject tissue except for the desired target ligand or epitope. To compare a control sample to a test sample, levels of light scattering can be detected by, for example, the systems described below and the difference in levels or location can be compared.

A targeting ligand can be coupled to the surface or shell of at least one of the nanoparticle. Targeted nanoparticles comprising targeting ligands can be produced by methods known in the art. For example ligands, including but not limited to, antibodies, peptides, polypeptides, or fragments thereof can be conjugated to the nanoparticle surface.

Any method known in the art for conjugating a targeting ligand to a nanoparticle may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982). Established protocols have been developed for the labeling metallic nanoparticles with a broad range of biomolecules, including protein A, avidin, streptavidin, glucose oxidase, horseradish peroxidase, and IgG (antibodies). Nanoparticles can be prepared with bioorganic molecules on their surface (DNA, antibodies, avidin, phospholipids, etc). The nanoparticles may be characterized, modified, and conjugated with organic and biomolecules. Polymers or other intermediate molecules can be used to tether antibodies or other targeting ligands to the surface of nanoparticles. Methods of tethering ligands to nanoparticles are know in the art as described in, for example, Loo et al., "Nanoshell-Enabled Photonics-Based Imaging and Therapy of Cancer," Tech. Cancer Res. and Treatment, (2004) 3(1) 33-40, which is incorporated herein by reference for the methods taught herein.

Covalent binding of a targeting ligand to a nanoparticle can be achieved, for example, by direct condensation of existing side chains or by the incorporation of external bridging molecules. Many bivalent or polyvalent agents are useful in coupling polypeptide molecules to other particles, nanoparticles, proteins, peptides or amine functions. Examples of coupling agents are carbodiimides, diisocyanates, glutaraldehyde, diazobenzenes, and hexamethylene diamines. This list is not intended to be exhaustive of the various coupling agents known in the art but, rather, is exemplary of the more common coupling agents that may be used.

Optionally, one may wish to first derivatize an antibody if used, and then attach the nanoparticle to the derivatized product. As used herein, the term "derivatize" is used to describe the chemical modification of the antibody substrate with a suitable cross-linking agent. Examples of cross-linking agents for use in this manner include the disulfide-bond containing linkers SPDP (N-succinimidyl-3-(2-pyridyldithio) propionate) and SMPT (4-succinimidyl-oxycarbonyl-α-methyl-α(2-pyridyldithio)toluene).

Targeting ligands may also be conjugated to nanoparticles using methods including the preparation of biotinylated antibody molecules and their consequent interaction with streptavidin/nanoparticle conjugates. This approach takes advantage of strong biospecific interaction between biotin and streptavidin and known protocols for immobilization of streptavidin on nanoparticles. Smaller polypeptide molecules may not be directly adsorbed on the nanoparticle surface because such binding could significantly change their conformation and lead to loss of binding properties. Polypeptides with thiol terminated alkyl chains may be directly attached to the surface of nanoparticles using the procedures described in Elghanian, R., et al., Selective calorimetric detection of polynucleotides based on the distance-dependent optical properties of gold nanoparticles. Science, 1997. 277(5329): p. 1078-1080 (incorporated by reference for the methods taught therein). For conjugation procedure one may use a mixture of thiol terminated polypeptides and relatively small mercaptoacetic molecules to avoid high density immobilization of the polypeptides.

Targeted nanoparticles can be prepared with a biotinylated surface and an avidinated antibody, peptide, polypeptide or fragment thereof can be attached to the nanoparticle surface using avidin-biotin bridging chemistry. Avidinated nanoparticles can be used and a biotinylated antibody or fragment thereof or another biotinylated targeting ligand or fragments thereof can be administered to a subject. For example, a biotinylated targeting ligand such as an antibody, protein or other bioconjugate can be used. Thus, a biotinylated antibody, targeting ligand or molecule, or fragment thereof can bind to a desired target within a subject. Once bound to the desired target, the nanoparticle with an avidinated surface can bind to the biotinylated antibody, targeting molecule, or fragment thereof. When bound in this way, light energy can be transmitted to the bound nanoparticle, which can produce light scattering of the transmitted light. An avidinated nanoparticle can also be bound to a biotinylated antibody, targeting ligand or molecule, or fragment thereof prior to administration to the subject.

When using a targeted nanoparticle with a biotinylated surface or an avidinated surface a targeting ligand can be administered to the subject. For example, a biotinylated targeting ligand such as an antibody, polypeptide or other bioconjugate, or fragment thereof, can be administered to a subject and allowed to accumulate at a target site When a targeted nanoparticle with a biotinylated surface is used, an avidin linker molecule, which attaches to the biotinylated targeting ligand can be administered to the subject. Then, a targeted nanoparticle with a biotinylated shell is administered to the subject. The targeted nanoparticle binds to the avidin linker molecule, which is bound to the biotinylated targeting ligand, which is itself bound to the desired target. In this way, a three step method can be used to target nanoparticles to a desired target. The targeting ligand can bind to all of the desired targets detailed above as would be clear to one skilled in the art.

Nanoparticles, including targeted nanoparticles, can also comprise a variety of markers, detectable moieties, or labels. Thus, for example, a nanoparticle equipped with a targeting ligand attached to its surface can also include another detectable moiety or label. As used herein, the term "detectable moiety" is intended to mean any suitable label, including, but not limited to, enzymes, fluorophores, biotin, chromophores, radioisotopes, colored particles, electrochemical, chemical-modifying or chemiluminescent moieties. Common fluorescent moieties include fluorescein, cyanine dyes, coumarins, phycoerythrin, phycobiliproteins, dansyl chloride, Texas Red, and lanthanide complexes. Of course, the derivatives of these compounds are included as common fluorescent moieties.

The detection of the detectable moiety can be direct provided that the detectable moiety is itself detectable, such as, for example, in the case of fluorophores. Alternatively, the detection of the detectable moiety can be indirect. In the latter case, a second moiety reactable with the detectable moiety, itself being directly detectable can be employed.

A composition, including at least one nanoparticle, may be administered to a subject orally, parenterally (e.g., intravenously), by intramuscular injection, by intraperitoneal injection, transdermally, extracorporeally, topically or the like. Parenteral administration of a composition, if used, is generally characterized by injection. Injectables can be prepared in conventional forms, either as liquid solutions or suspensions, solid forms suitable for solution of suspension in liquid prior to injection, or as emulsions.

The compositions, including nanoparticles, can be used in combination with a pharmaceutically acceptable carrier. By "pharmaceutically acceptable" is meant a material that is not biologically or otherwise undesirable, i.e., the material may be administered to a subject, along with the nanoparticle, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5.0 to about 8.0, and more preferably from about 7.0 to about 7.5. As described above compositions can be administered intravascularly. Administered compositions may include carriers, thickeners, diluents, buffers, preservatives, surface active agents and the like in addition to the composition of choice. Administered compositions may also include one or more active ingredients such as antimicrobial agents, anti-inflammatory agents, anesthetics, and the like.

When used in the described methods, an effective amount of one of the compositions, including the nanoparticles, of the present invention can be determined by one skilled in the art. The specific effective dose level for any particular subject will depend upon a variety of factors including the type and location of the target site, activity of the specific composition employed, the specific composition employed, the age, body weight, general health, sex and diet of the subject, the time of administration, the route of administration, the rate of excretion of the specific composition employed, the duration of the treatment, drugs used in combination or coincidental with the specific composition employed, and like factors well known in the medical arts. For example, it is well within the skill of the art to start doses of the composition at levels lower than those required to achieve the desired diagnostic effect and to gradually increase the dosage until the desired effect is achieved. If desired, an effective dose may be divided into multiple doses for purposes of administration.

Depending on the above factors, on the composition used, on the intended target site for the composition, and whether active or passive targeting of the described compositions is used, the time between administration of the described compositions and the detection of the described nanoparticles within the subject may vary. For example, detection of the described nanoparticles may be performed at one or more time seconds, minutes, hours, days, and/or weeks after administration of the compositions to the subject. When and how frequently methods of detection of an administered composition are performed can be determined by one skilled in the art through routine administration and detection.

Alternatively, the nanoparticle comprising a material with non-zero magnetic susceptibility can be heated in vivo or in vitro by an applied magnetic field. A material of non-zero magnetic susceptibility can include a variety of materials. For example, the nanoparticle can comprise any physiologically tolerable magnetic material or combinations thereof. The term magnetic material means any material displaying ferromagnetic, paramagnetic or superparamagnetic properties. For example, the nanoparticles can comprise a material selected from the group consisting of iron oxide, iron, cobalt, nickel, and chromium. Optionally, a nanoparticle comprises iron oxide. When a nanoparticle comprises metal or magnetic materials, it can be moved while in the subject using an internally or externally applied magnetic field, as described below. Any relevant metal with non-zero magnetic susceptibility or combinations thereof can be used. Such relevant metals are known in the art. Nanoparticles can also comprise polymers or other coating materials alone or in combination. Such polymers or coating materials may be used to attach targeting ligands, including but not limited to antibodies, as described below. When used in vivo, an administered nanoparticle is physiologically tolerated by the subject, which can be readily determined by one skilled in the art.

Alternatively, Surface Plasmon Resonance ("SPR") heating wherein the particles are coated with a wavelength resonance specific coating to excite them, as described in Hawes et al., Journal of Quantitative Spectroscopy & Radiative Transfer 104 (2007) 199-207, herein incorporated by reference. In one embodiment of the invention, the nanoparticles are coated with a gold coating to excite the nanoparticles. The fusing of nanosized metallic particles occurs by melting the surface of the particles. In order to heat the particles selectively and locally, they are excited at their SPR. In order to selectively target nanoparticles, the amount of energy to melt the surface of the particles is required. The SPR wavelength is determined by a nanostructure's dielectric constant, geometry, and surrounding environment. Gold nanostructures with spheres smaller than 20 nm behave much like dipoles, with maximum absorption and scattering occurring at wavelengths near 500 nm in air or vacuum. Silver nanostructures exhibit similar behavior with the various resonances occurring at different wavelengths (about 350 nm) due to the dielectric constant dispersion of silver. This forms the basis for shape and material selectivity a nanoscale self-assembly system. Inter-particle spacing, material choice, and SPR play roles in the selective nature of directed assembly and direct solutions for Maxwell's equations are required.

With the calculation of the SPR particular to a metal, the differences in peak resonance for selectivity can be used. For gold, copper, and silver nanoparticles, whose resonance frequencies occur in the near UV and visible spectral regions, the resonance can be used to excite the particles. These particles can be excited selectively, i.e. gold and silver on the same surface and an incident light source at 500 nm, then only the gold will strongly absorb the light. Additionally, resonance wavelength varies with particle size. As particles increase in size toward 100 nm diameters their resonances shift toward the red portion of the spectrum. Thus, the type of particle (gold, silver, copper and other metals in the non-visible spectrum) and the size of particle that experiences resonance can be controlled. This control allows for precise patterning techniques in terms of size and material.

One exemplary particle comprises iron oxide and gold. The iron oxide can form a core that is surrounded partially or fully by a gold layer. Dextran can be applied to the gold layer to comprise a particle of iron, gold and dextran. Other exemplary layers can also be used. For example, a metallic core can selected based on its magnetic properties so that it can be moved in the subject by an applied magnetic force. A second metal layer can be selected based on that layer can modify the light absorption properties of the particle and the light absorptive characteristics of the tissue or media where the particle is located. For example, gold particles or shells can be used to absorb near infrared light. Exemplary combinations of materials for particles that can be moved by an applied magnetic force and can absorb light more than proximate tissue or cells of the subject can be selected using the principles of photothermolysis known in the art and described below.

Exemplary multifunctional OCT nanoparticle with an iron core for magnetic properties, a gold coating to tune wavelength absorption to 700 nm (above competing plaque components), and an adsorbed aminodextran coating for enhanced selective macrophage uptake. Exemplary multifunctional OCT nanoparticles (MONs) with an aminodextran outer shell adsorbed on an inner gold shell. Additional $NH_2$ sites on the dextran that are not bound to gold can be used to conjugate small molecules such as Glycine to raise the selectivity for macrophage uptake. Particle shape can also be altered to mimic the rod-like appearance of bacteria to enhance macrophage uptake. Exemplary nanoparticles comprising, for example, iron oxide cores with gold shells can be used, which can absorb at about 700 nm. An outermost coating comprising dextran with a particle diameter less than 40 nm can be used to reduce uptake by liver and spleen, thereby prolonging blood circulation time to increase plaque based macrophage uptake.

Superparamagnetic iron oxide nanoparticles (SPION) consist of a small (<10 nm) iron oxide core coated with silicon or dextran. Iron oxide cores are water soluble and both magnetite ($Fe_3O_4$) and maghemite (—$Fe_2O_3$) have been used as a core material. FERIDEX (AMI-25, ENDOREM®) was used as SPIO in this study. FERIDEX is composed of a 5 nm iron oxide core and nanoparticle size is 150 nm including a dextran coating. Concentrations of SPIO solutions in our studies were 1.4, 2.8, 5.6 and 11.2 mg/mL. Mono crystalline iron oxide nanoparticles (MION) may be used as an ultrasmall superparamagnetic iron oxides nanoparticles ("USPIO"). MION is a superparamagnetic intravascular contrast agent with an average core size of 4-7 nm and has a 30 nm diameter including the dextran coating. Core diameter (<10 nm) of SPIO and MION are less than the size of a single magnetic domain (15 nm for Fe) and thus both nanoparticles are superparamagnetic.

Ultrasmall paramagnetic iron oxide (USPIO) nanoparticles were designed for selective macrophage uptake, highly sensitive phase-sensitive Fourier-domain magnetomechanical OCT imaging, and tunable near infrared photothermolysis of macrophages. The particles can comprise an iron oxide core for magnetic properties coated with a gold shell for near infrared absorption, and an outer coating of dextran for selective uptake by macrophages. A composite diameter less than 40 nm can be used to minimize uptake into the liver and spleen and prolong blood half-life. To further enhance selective macrophage uptake, the dextran coating can be decorated with small molecules such as glycine. The inner gold shell can be about 1-8 nm thick and can be located between an iron oxide core of approximately 5 nm, and an outer dextran shell. The surface plasmon resonance of the gold shell can absorb strongly in the near infra-red at about 700 nm where tissue transmissivity is high due to relatively low scattering and absorption. Since plaque components including water, arterial tissue, and lipid maximally absorb at about 500-600 nm, the gold can be used for particles with selective absorption greater than surrounding plaque components. The gold shell can be attached to the dextran coating (with or without decoration by small molecules such as glycine) to target macrophages in vulnerable plaques The particles can be synthesized by reaction of a mixture of Fe(III) and Fe(II) with 1.0 M NaOH at 80° C. for 30 min. in the presence of a surfactant Triton X-100. The inhibition of particle agglomeration by Triton X-100 micelles was found to produce a uniform particle size on the order of 13+0.5 nm. After reaction, the particles can be separated by centrifugation and washed. Next, the particles can be coated with gold shells produced by reduction of a 10-2 M $HAuC_{14}$ solution with glucose. The use of a mild reducing agent, glucose, for the adsorbed Au(1~I) ions on the Fe3O4 particles can be used to control shell thickness from 4 to 8 nm, by varying the ratio of Fe3O4 to Au(1YI). These particles have a large magnetic permeability at 300 K of 2 to 8 emu/g, and can be used for magneto-motive OCT.

Dextran, can be modified with amine groups, and can be adsorbed onto the inner gold shells. Aminodextrans are available commercially, for example, from Molecular Probes (Carlsbad, Calif.) at including, 10, 40, 70 and 500 k MW. Aminodextrans can also be synthesized by an established technique to vary the degree of amination per dextran monomer from about 1:5 to about 1:40. The sugar rings in dextran can be oxidized with periodate, $NaIO_4$, to produce aldehyde functionalities. The resulting —RHC=O can be reacted with 1,3-diaminopropane to form a Schiff's base —RC=N—$C_3H_6NH_2$. This base can then be reduced with $N_aBH_4$ to form a stable —RC—N—$C_3H_6NH_2$ linkage and to reduce unreacted aldehydes in dextran back to alcohols.

In an alternative exemplary approach for stronger attachment, dextran can be linked covalently to the gold shell on the nanocrystals. The gold can be aminated with 11-amino-1-undecanethiol, $NH_3$+Cl($CH_2$)11SH. The thiol group can bind strongly to gold. The amino groups on the surface of the gold can be reacted with dextran, which can be partially oxidized by NaIO4. The reaction of the resulting RHC=O (on dextran) with the R'$NH_2$ groups on gold produces a Schiff's base, RC=N—R'. This base can then be reduced with $NaBH_4$ to form a stable R—C—N—R' linkage and to reduce unreacted aldehydes in the dextran back to alcohols.

In a third exemplary alternative, the alcohol functionalities on dextran can be reacted with gold, modified with epoxy surface groups. The epoxy groups can be formed by reaction of chlorohydrin with gold stabilized by 16-mercaptohexadecanoic acid. Although dextran is selective for macrophages, higher selectivity's can be achieved by modification of the particles. For example, dextran-coated cross-linked iron oxide magnetic nanoparticles can be decorated with a library of small molecules for cell-targeting. For example, the addition of glycine can be used to enhance selectivity of the nanoparticles for activated macrophages. The particles can, however, be modified with various acids and anhydrides including glycine, L-valine, LAsparagine, citraconic anhydride and acetic anhydride. The synthetic procedures for conjugation of these species are known in the art. The carboxylic acids can be conjugated to aminated dextran in a morpholinoethanesulfonic acid buffer at pH 6.0. The anhydrides can be conjugated in a bicarbonate buffer at pH 8.5. The products can be purified by gel filtration with a Sephadex® G-25 column. The degree of conjugation can be determined by the loss of amine groups. Because typical reagents for determining amine concentrations can be incompatible with iron oxide and ferric and ferrous ions, a procedure based on Nsuccinimidyl 3-(2-pyridyldithio)-propionate (SPDP) can be used. After reaction with SPDP, the product can be separated from the nanocrystals and analyzed to determine the loss of amine groups, and thus the degree of conjugation. The gold can be coated directly with aminated dextran, which can then be decorated with the small molecule for macrophage targeting. In the two exemplary alternative approaches, where the gold is coated with dextran, the dextran can be cross-linked with epichlorohydrin and aminated with ammonia and then modified.

Thermal Imaging Apparatus

FIG. 1 is a schematic view of the thermal imaging apparatus 10. The thermal wave imaging apparatus 10 generally includes a catheter body 20, a thermal sensor 30, and a laser-heating element 40. The catheter body 20 is optically coupled to a conduit 22, for transmitting optical energy to the laser heating element 40 and electrical energy to and from the thermal sensor 30. The catheter body 20 permits the thermal wave imaging apparatus 10 to pass through a lumen of a subject's body. The catheter encompasses various types of general catheters known in the medical arts. Such catheter examples include over the wire catheters, balloon catheters, atherectomy catheters, stent delivery catheters, percutaneous myocardial revascularization catheters, and the like. The conduit 22 is optically coupled to an optical light source through an optical fiber and a thermal reading source through a lead wire. As used herein, optical fiber can refer to glass or plastic wire or fiber. Optical fiber is indicated on FIG. 4 as lines connecting the various blocks of the figures. Where light energy is described as "passing," "traveling," "returning," "directed," or similar movement, such movement can be via optical fiber.

The thermal sensor 30 is operably coupled to the proximal portion of the catheter body 20, as to permit optical energy to pass through the thermal sensor 30 to the laser heating element 40. In one embodiment of the invention, the thermal sensor 30 is positioned circumferentially about the longitudinal axis of the catheter body 20. The laser heating element 40 includes a reflective element 42 to permit the optical energy from optical conduit to reflect about a 360 degree rotation 46. The reflective element 42 rotates about an axis by a rotation element 44. Such a rotational element 44 can be any turbine type mechanical device known in the art. A turbine-type device is described in Patent Cooperation Treaty application PCT/US04/12773 filed Apr. 23, 2004 which claims priority to U.S. provisional application 60/466,215 filed Apr. 28, 2003, each herein incorporated by reference for the methods, apparatuses and systems taught therein. Alternatively, the optical fiber 22 can rotate about an axis with the reflective element 42 located therein, to allow for the 360 rotation to heat a blood vessel. Such a rotatable optical fiber is generally known, whereby the optical fiber rotates about an axis and is coupled to a ferrule and a prism for reflecting light about a 360 rotation.

The thermal sensor 30 may be coupled to any kind of a temperature sensor, as known to one skilled in the electrical arts. In one embodiment, the thermal sensor 30 is a thermocouple. Thermocouples are a widely used type of temperature sensors and can be used as a means to convert thermal potential difference into electric potential difference. Alternatively, the thermal sensor may be a thermistor, microthermistor, infra red sensor, and the like. A thermistor is a type of resistor used to measure temperature changes, relying on the change in its resistance with changing temperature. Alternatively, the thermal sensor 30 may be microbolometer array, which is a grid of vanadium oxide or amorphous silicon heat sensors atop a corresponding grid of silicon. The sensors are suspended atop a very thin micro structure, and trapped within a vacuum. Infrared radiation from a specific range of wavelengths strikes the vanadium oxide, heating it, and thus changing its electrical resistance. This resistance change is measured and processed into temperatures. The microbolometer grid is commonly found in two sizes, a 320×240 array or less expensive 160×120 array, which is fabricated by micromachining processes, i.e. photolithography, etching, etc.

In another embodiment, the thermal sensor is operably coupled to an infrared camera. The infrared camera uses infrared radiation to generate an image using visible light. Alternatively, the thermal sensor can be infrared radiation sensors, which can be electrically coupled to an electrical wire to transmit the infrared radiation signal to an infrared camera device. Generally speaking, the thermal sensor would be enabled to image the heat generated by the heated nanoparticles at high resolution. The thermal sensors could be mounted circumferentially around the catheter body, or could be mounted on one side of the catheter body along with a rotational element to permit a 360 degree rotation about an axis.

Figure 3:
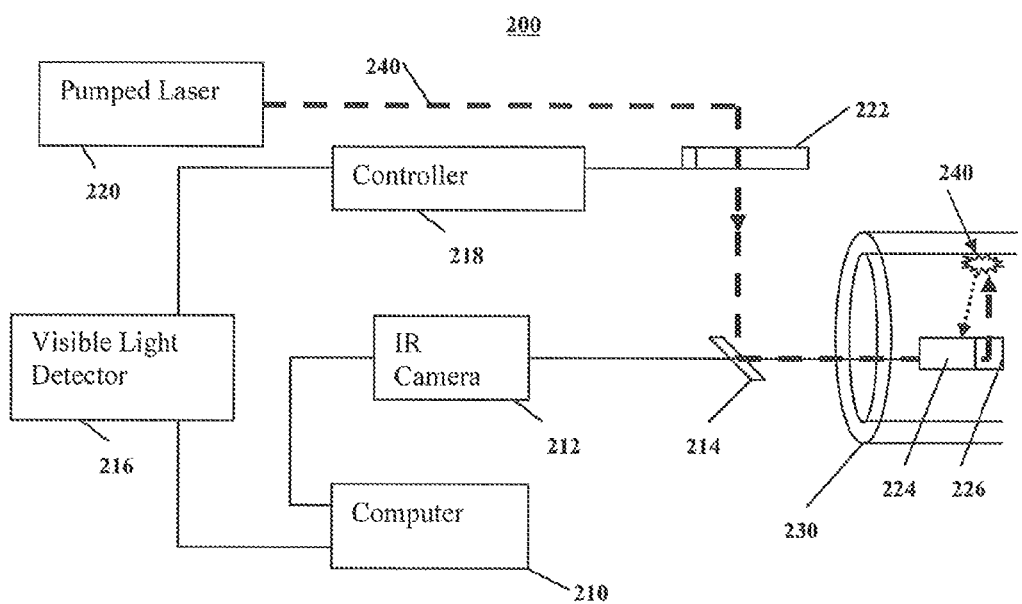
FIG. 3 is a schematic diagram illustrating a representative thermal wave imaging embodiment of the present invention.

The thermal sensor could be selected to have linearity between the degree changes of the macrophages in a vulnerable plaque. As an example, the thermal sensor could be sensitive to 35° C. and 45° C. and maintain a resolution of 0.01° C. to 0.10° C. The thermal sensor is operably connected to an electrical wire, to provide an electrical connection to a computing device, as shown in FIG. 3. The temperature data is received by the computer and processed by system software and digital converters to generate a thermal image, as shown in FIGS. 2A and 2B. The processing of the thermal image is similar in the processing of an OCT image, as detailed below, i.e. overlaying a false-color macrophage density map over the 2D or 3D artery image.

In one embodiment, a pull back mechanism 50 is employed to permit the thermal sensor to detect the heated nanoparticles once the laser heating element has sufficiently heated the nanoparticles, as shown in FIG. 1. The pull back mechanism can be a manual pull back by an operator, or an electronic motor device to pull back the catheter body. Such a device would include a mount for the conduit of the catheter body, which is in a fixed position relative to the movable catheter body. An electronic motor would be operably coupled to the catheter body, as to pull back the catheter body once the laser heating element has heated the nanoparticles to a sufficient temperature.

The thermal imaging system 200 can be generally understood by FIG. 3, where the thermal imaging system 200 comprises a thermal sensor 224 and a laser-heating element 226 operably coupled to an infrared camera 212 and a computer 210. The computer 210 is operably coupled to a visible light detector 216. The visible light detector 216 is coupled to a 10 Hz frequency controller 218 to monitor the laser pulses emitted by laser 220 through an electronic shutter 222. The visible light detector may be a photoreceiver to detect the modulated laser intensity (New Focus, San Jose, Calif.). In one embodiment of the invention, the laser 220 emits pulsed energy 240 at a wavelength of 532 nm through the electronic shutter 222 to mirror 214 to be reflected off the laser heating element 226 to the nanoparticles 240 incorporated into macrophages of an artery 230. The nanoparticles 240 are heated and the infrared emission is detected by a thermal sensor 224 coupled to the infrared camera 212, whose signal generates a thermal image on computer 210. A sinusoidal signal in-phase with the detected laser intensity was generated using a low pass filter. The sinusoidal signal was Hilbert transformed and quadrature reference signals, real and imaginary, were generated. The reference signals were used to compute amplitude and phase for thermal wave imaging. The IR camera 212 records IR images at 100 frames per second from the irradiated nanoparticles. An individual image is low pass filtered by a 2D convolution with a 3×3 pixel rectangular image block to increase a signal-to-noise ration by removing a shot noise and repeated for all recorded image frames. The filtered sequential array of modulated IR emission intensity at each pixel is multiplied by the real and imaginary values of the processed IR emission at each pixel were obtained for thermal wave imaging. Magnitude and phase at each pixel were calculated and the thermal wave image is constructed.

The computer 210 is coupled with a data interface to the thermal imaging system 200, which can be a Universal Serial Bus, or the like. The data from the thermal sensor 224 can be provided in analog or digital signals, whereby an analog to digital converter would be required for an analog signal. The thermal sensor 224 data can be stored in a sass storage device or system memory of the computer 210 and utilized thermal image construction software, Labview image construction software, and the like.

The laser source 220 can be a pulsed laser light source coupled into the optical fiber emitting light energy over a broad range of optical frequencies, as shown in FIG. 3. For example, the range can be from about 400 nanometers to about 1400 nanometers. Pulsed laser light sources are pulsed lasers generating picosecond and femtosecond fundamental and second harmonic light pulses in 400-1400 nanometer region, and are generally known in the art. Laser pulses at longer wavelength (>600 nm) can be used for deeper scanning. In one embodiment, the light source emits pulsed laser light having a wavelength near the absorptive spectrum of nanoparticles localized in macrophages, as to heat the nanoparticles to a temperature sufficient to enhance the contrast between the macrophage containing plaques and the surrounding tissue. The light energy can be emitted over a multiplicity of optical wavelengths, frequencies, and pulse durations to achieve optical nanoparticle heating and thermal wave imaging. The combination of light energy and nanoparticle composition can be selected from a multitude of combinations to elicit optimal energy absorption and emission properties. The nanoparticles can be coated with compositions that aid in the selective absorption of the light energy. The emission of heat energy can further be modulated by selecting nanoparticle composition(s) that re-emit or fluoresce at frequencies that are optimal for detection by the thermal or optical sensors. If the operator desires to minimize the heat transfer to the macrophage and surrounding tissue, on could select nanoparticle compositions that have low heat capacity and therefore reduce the amount and duration that the absorbed energy is emitted heat (or other energy signal). Close coupling of the energy transmitting and energy sensing apparatus on the catheter would minimize the amount of energy transfer required in such a system. Alternatively, the use of fluorescent nanoparticles would enable selective detection of the macrophages without the transfer of significant energy to the surrounding tissue.

Figure 4:
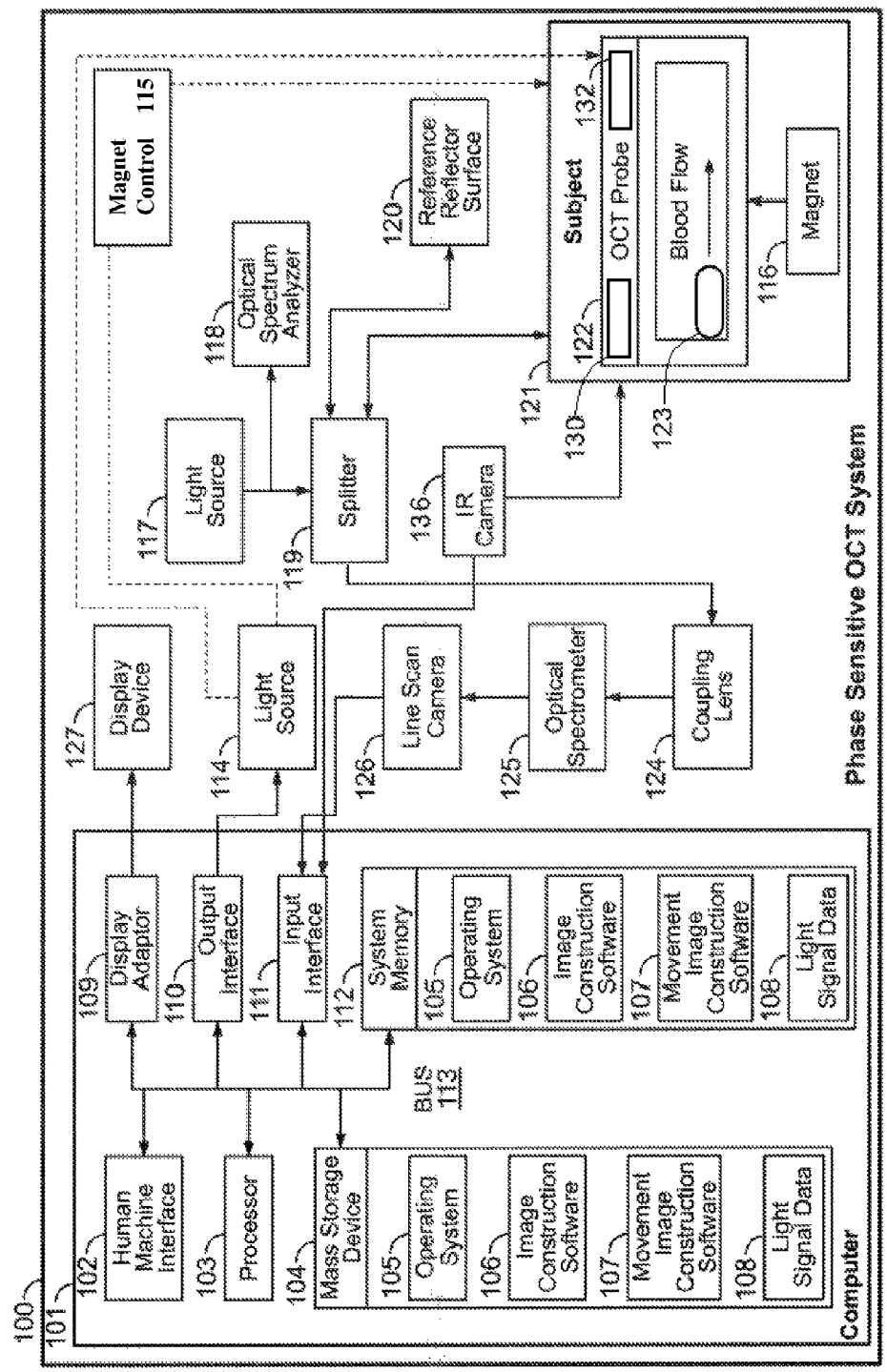
FIG. 4 is a block diagram illustrating an exemplary phase sensitive OCT system.

Alternatively, the heating element may be a magnetic field produced by a magnet, as shown in FIG. 4. The nanoparticles can be selected as to respond to a magnetic field and cause an increase in temperature, which is then recorded by the thermal sensor.

Thermal Wave Imaging Method

Methods and apparatuses for identifying vulnerable plaques by administering a plurality of metallic nanoparticles to a subject, heating at least one nanoparticle, and imaging the heated nanoparticle with a thermal sensor. Optionally, at least one administered nanoparticle localizes within a macrophage located in the subject. At least one administered nanoparticle can also be optionally configured to localize to a target site in the subject.

Methods of identifying a vulnerable plaque comprising (1) administering a plurality of metallic nanoparticles to a subject; (2) heating at least one administered nanoparticle; and (3) imaging the heated metallic nanoparticles with a thermal sensor.

Alternatively, the method includes localizing at least one administered nanoparticle within a macrophage located within the subject. Alternatively, the method includes configuring at least one nanoparticle to localize to a target site in the subject.

The method further comprises generating light energy, reflecting the light energy of a mirror, and rotating the mirror element in a 360 degree arc. Alternatively, the light energy could be propagated from a plurality of fibers, producing a radial pattern. Alternatively, the light energy could be generated from a single fiber but divided by means of a conical reflector at the end of the fiber to produce the radial distribution. Similarly, a diffraction grating could be used to distribute the light. The angle of the light could be perpendicular to the axis of the fiber, but could also be adjusted to "look forward" or "look backward". (In the case of distributing the non-imaging light (i.e., pulsed laser), the lens' and reflective parameters are less complicated, since the purpose is just to heat, not forming an image.)

The method further comprises coupling the catheter to an optical coherence imaging system, whereby at least a portion of transmitted first portion of light energy.

The heating of the nanoparticle can be accomplished by a variety of methods. In one embodiment, the step of heating the nanoparticle includes generating an optical energy; transmitting optical energy through a catheter body; reflecting the optical energy through a reflective element; and rotating the reflective element. A pulsed laser tuned to the wavelength of the absorptive spectrum of the nanoparticle. Alternatively, the heating of the nanoparticle includes applying a magnetic field to the nanoparticle.

Such heating of the nanoparticle above an ambient temperature enhances the contrast between the macrophage containing plaques and the surrounding tissue. By taking known techniques of heating nanoparticles, as indicated above, an enhanced contrast image of macrophages in vulnerable plaques can be detected.

The method further comprises coupling the thermal wave imaging apparatus with an OCT system; whereby a pulsed laser source generates an OCT image of the macrophages, and the thermal imaging apparatus generates a thermal image of the vulnerable macrophages.

OCT System

The thermal imaging apparatus 10 may be used alternatively with an optical coherence tomography system 100, as shown in FIG. 4. As such, the OCT image can be overlaid the thermal image generated by the thermal wave imaging apparatus 10. Generally speaking, the laser heating element 40 would be coupled to an OCT probe 122 to produce OCT three dimensional images of the arterial wall to aid in the location of the thermal wave imaging apparatus near a plaque. The OCT system can be readily understood by provisional application 60/685,559, herein incorporated by reference. These exemplary OCT systems are only examples of phase sensitive spectral domain OCT systems and are not intended to suggest any limitation as to the scope of use or functionality of OCT architectures. Neither should the OCT systems be interpreted as having any dependency or requirement relating to any one or combination of components illustrated in the exemplary OCT systems The detection and heating of the administered nanoparticles in the subject's tissue, or in vitro, using optical coherence tomography comprises generating light energy and transmitting at least a first portion of the generated light energy onto a reference reflector and at least a second portion of the generated light energy into the subject's tissue.

At least a portion of the transmitted first portion of light energy is reflected by the reference reflector. Optionally, at least a portion of the transmitted second portion of light energy contacts at least one nanoparticle located within a macrophage and/or at least a portion of the transmitted second portion of light energy contacts at least one nanoparticle that is localized to a target site in the subject. At least a portion of the transmitted second portion of light energy contacts the subject's tissue. At least a portion of the light energy which contacts a nanoparticle and at least a portion of the light energy which contacts the subject's tissue are reflected.

The method further comprises receiving the light energy reflected by the reference reflector, the subject's tissue and the at least one nanoparticle and combining the received light energy, wherein the combined light energy interferes. The combined light energy is processed to produce a phase sensitive optical coherence tomography image of the nanoparticle and macrophage.

A Phase Sensitive OCT system 100 can be used to image the blood flow, when an oscillating magnetic field is applied to a biological sample, as shown in FIG. 4. This OCT system 100 is only an example of one OCT system which can be used to image blood flow with a temporally oscillating magnetic field, and is not intended to suggest any limitation on the scope of OCT architectures applicable to the invention. The OCT system 100 includes a general-purpose computing device in the form of a computer 101. The Phase Sensitive OCT system 100 can also include a magnet control 115 and a magnet 116. The OCT probe generally includes a catheter with the thermal imaging apparatus 10, with the thermal sensor 130 operably coupled to an IR Camera 136 and a laser heating element 132 optically coupled to a light source 114, as described previously. The IR Camera 136 is coupled to the input interface 111 of the computer 101 to process thermal wave images as described previously.

Light energy is generated by a light source 117. The light source 117 can be a pulsed laser light source coupled into optical fiber emitting light energy over a broad range of optical frequencies. For example, the range can be from about 400 nanometers to about 1400 nanometers. Pulsed laser light sources are pulsed lasers generating picosecond and femtosecond fundamental and second harmonic light pulses in 400-1400 nanometer region, and are generally known in the art. Laser pulses at longer wavelength (>600 nm) can be used for deeper scanning. Preferably, the light source emits pulsed laser light having a wavelength near the infrared spectrum to identify macrophages for OCT imaging, which places hemoglobin in motion and increases optical scattering of the hemoglobin. The light energy can be emitted over a multiplicity of optical wavelengths, frequencies, and pulse durations to achieve OCT imaging. As used herein, optical fiber can refer to glass or plastic wire or fiber. Optical fiber is indicated on FIG. 4 as lines connecting the various blocks of the figures. Where light energy is described as "passing," "traveling," "returning," "directed," or similar movement, such movement can be via optical fiber.

A fraction of the generated light energy passes from the light source 117 into an optical spectrum analyzer 118. The optical spectrum analyzer 118 measures optical frequency as the light energy is emitted from the light source 117 as a function of time. The optical spectrum analyzer 118 samples a portion of the light emitted by the light source 117. The optical spectrum analyzer 118 monitors the power spectral density of light entering the splitter 119. The remaining fraction of light energy from the light source 117 passes into a splitter 119. The splitter 119 can be a device with four ports, with Port 1 allowing light energy to enter the splitter 119. Ports 2 and 3 allow light energy to leave and re-enter the splitter 119 to the reference reflector 120 and OCT probe 122, respectively. Port 4 allows light energy to leave the splitter 119 to coupling lens 124. The splitter 119 couples the light into Port 1. The splitter 119 divides the light according to a pre-determined split ratio selected by a user. For example, the split ratio can be 50/50 wherein half of the light energy entering the splitter 119 at Port 1 exits the splitter 119 through Port 2 and half exits the splitter 119 through Port 3. In another example, the split ratio can be 60/40 wherein 60% of the light energy passes through Port 2 and 40% of the light energy passes through Port 3.

A fraction of the light energy (determined by the split ratio) that exits the splitter 119 through Port 2 travels to a reference reflector surface 120. The light energy is reflected from the reference reflector surface 120 back to the splitter 119 into Port 2. The reference reflector 120 can be a planar metallic mirror or a multilayer dielectric reflector with a specified spectral amplitude/phase reflectivity. The remaining fraction of light that entered splitter 119 through Port 1 exits splitter 119 through Port 3 and enters an OCT probe 122. The OCT probe 122 can be a turbine-type catheter as described in Patent Cooperation Treaty application PCT/US04/12773 filed Apr. 23, 2004 which claims priority to U.S. provisional application 60/466,215 filed Apr. 28, 2003, each herein incorporated by reference for the methods, apparatuses and systems taught therein. The OCT probe 122 is operably coupled to the laser heating element 132, to provide optical energy to both image a blood vessel and generate optical energy to heat the nanoparticles 123. Alternatively, a separate light source 114 is used to heat the nanoparticles 123.

The light energy that entered OCT probe 122 is reflected off of the blood flow, blood vessels, or the nanoparticles 123 of a subject 121. Alternatively, an oscillating magnetic field can be temporally applied by magnet 116 to provide increased heat or image contrast of the nanoparticles 123. The reflected light energy passes back through the OCT probe 122 into the splitter 119 via Port 3. The reflected light energy that is returned into Port 2 and Port 3 of the splitter 119 recombines and interferes according to a split ratio. The light recombines either constructively or destructively, depending on the difference of pathlengths. A series of constructive and destructive combinations of reflected light create an interferogram (a plot of detector response as a function of optical path length difference ($c\tau$) or optical time-delay($\tau$)). Each reflecting layer from the subject 121 and the nanoparticles 123 will generate an interferogram. The splitter 119 can recombine light energy that is returned through Port 2 and Port 3 so that the light energies interfere. The light energy is recombined in the reverse of the split ratio. For example, if a 60/40 split ratio, only 40% of the light energy returned through Port 2 and 60% of the light energy returned through Port 3 would be recombined. The recombined reflected light energy is directed out Port 4 of the splitter 119 into a coupling lens 137. The coupling lens 137 receives light from the output of the splitter 119 and sets the beam etendue (beam diameter and divergence) to match that of the optical spectrometer 125. The coupling lens 124 couples the light into an optical spectrometer 125. The optical spectrometer 125 can divide the recombined reflected light energy light into different optical frequencies and direct them to different points in space which are detected by a line scan camera 126. The line scan camera 126 performs light to electrical transduction resulting in digital light signal data 108. The digital light signal data 108 is transferred into the computer 101 via the input interface 111. Interface between the line scan camera 126 and computer 101 can be a Universal Serial Bus (USB), or the like. The digital light signal data 108 can be stored in the mass storage device 104 or system memory 112 and utilized by the image construction software 106 and the Labview image construction software 107.

The system bus 113 represents one or more of several possible types of bus structures, including a memory bus or memory controller, a peripheral bus, an accelerated graphics port, and a processor or local bus using any of a variety of bus architectures. By way of example, such architectures can include an Industry Standard Architecture (USA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus. This bus, and all buses specified in this description can also be implemented over a wired or wireless network connection. The bus 113, and all buses specified in this description can also be implemented over a wired or wireless network connection and each of the subsystems, including the processor 103, a mass storage device 104, an operating system 105, an image construction software 106, a nanoparticle movement image construction software 107, light signal data 108, the system memory 112, an OCT input interface 111, an OCT output interface 110, a display adapter 109, a display device 127, a human interface device 102, and a digital image capture device, can be contained within one or more remote computers (not shown) at physically separate locations, connected through buses of this form, in effect implementing a fully distributed system.

The computer 101 can include a variety of computer readable media. Such media can be any available media that is accessible by the computer 101 and includes both volatile and non-volatile media, removable and non-removable media. The system memory 112 includes computer readable media in the form of volatile memory, such as random access memory (RAM), and/or non-volatile memory, such as read only memory (ROM). The system memory 112 typically contains data such as light signal data 108 and/or program modules such as operating system 105, image construction software 106 and nanoparticle movement (or cellular membrane tension level or internal strain field change) image construction software 107 that are immediately accessible to and/or are presently operated on by the processing unit 103. Throughout this application the disclosed methods, compositions and apparatuses for detecting a cell and/or a metallic composition are described herein variously by reference to metallic particle movement.

Any number of program modules can be stored on the mass storage device 104, including by way of example, an operating system 105, image construction software 106, nanoparticle movement (or cellular membrane tension level or internal strain field change) image construction software 107, thermal image data construction software, thermal data, and light signal data 108. Each of the operating system 105, image construction software 106, nanoparticle movement (or cellular membrane tension level or internal strain field change) image construction software 107, thermal image construction software, thermal data, light signal data 108 (or some combination thereof) can include elements of the programming image construction software 106 and the nanoparticle movement (or cellular membrane tension level or internal strain field change) image construction software 107.

A user can enter commands and information into the computer 101 via an input device (not shown). Examples of such input devices include, but are not limited to, a keyboard, pointing device (e.g., a "mouse"), a microphone, a joystick, a serial port, a scanner, and the like. These and other input devices can be connected to the processing unit 103 via a human machine interface 102 that is coupled to the system bus 113, but can be connected by other interface and bus structures, such as a parallel port, game port, or a universal serial bus (USB).

A display device 127 can also be connected to the system bus 113 via an interface, such as a display adapter 109. For example, a display device can be a monitor. In addition to the display device 127, other output peripheral devices can include components such as speakers (not shown) and a printer (not shown) which can be connected to the computer 101 via an input/output interface (not shown).

The image construction software 106 can generate an image of the blood vessels of subject 121 from the light signal data 108, by receiving light signal data 108 generating amplitude and phase data. The amplitude and phase data (optical path length difference ($c\tau$) or optical time-delay ($\tau$)) can be separated into discrete channels and a plot of intensity vs. depth (or amplitude vs. depth) can be generated for each channel. Such plot is known as an A-scan, where the composition of all the A-scans can comprise one image. And movement image construction software 107 generates an image of the blood vessels from the light signal data 108. The movement image construction software 107 receives light signal data 108 for the reflected light from the light source 117 or the light source performs a Fourier transform on the light signal data 108 generating amplitude and phase data.

An implementation of the image construction software 106 and the nanoparticle movement (or cellular membrane tension level or internal strain field change) image construction software 107 can be stored on or transmitted across some form of computer readable media. Computer readable media can be any available media that can be accessed by a computer. By way of example, and not limitation, computer readable media can comprise "computer storage media" and "communications media." "Computer storage media" include volatile and non-volatile, removable and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The light signal data 108 can enter the computer 101 via the OCT input interface 111. The OCT output interface can be IEEE-488, IEEE-1 394, Universal Serial Bus (USB), or the like. The light signal data 108 can be stored in mass storage device 104 and transferred to system memory 112 as light signal data 108 to be used by image construction software 106 and nanoparticle movement (or cellular membrane tension level or internal strain field change) image construction software 107.

Alternatively, the phase sensitive OCT system 100 can be configured for swept source OCT, which is a different type of spectral domain OCT. In swept source OCT, a tunable laser source replaces the broadband laser light source 117. The scanning rate can be at wavelengths of 800 nm-1500 nm. Also, the reference reflector surface 120 is in-line with sample path 120. The optical spectrometer 125 and line scan camera 126 are replaced with a general photodetector. In this configuration, an optical clock is used to trigger acquisition of the signal produced by the photodetector. The optical clock provides a set of uniformly spaced clock pulses with fixed intervals of optical frequency and at least one reference pulse. The fixed intervals of optical frequency are configured and specified in the optical clock to give a uniform train of pulses. The at least one reference pulse generated by the optical clock is utilized to provide a reference optical frequency or a trigger pulse. For example, the first reference pulse generated by the optical clock can correspond to an absorption line in a gas cell (e.g., Hydrogen Fluoride or Hydrogen Bromide). In this case the gas absorption line has a known optical frequency. The well-known absorption fingerprint bands in the HF gas cell result in a reduced detected intensity in the light transmitted through the gas cell, and as such provide a metric on the absolute lasing wavelength at the digitized samples of the photodetector signal. The digitized sample number or sampling time scale can thus be converted to absolute wavelength at one or more samples, depending on the number of absorption lines. The detected wavemeter photocurrent signal and the detected gas cell photocurrent signal are combined in the digitizer to provide the relationship between the sample number or sampling time and lasing wavelength throughout the entire sweep. The detected photocurrent signal from the gas cell is digitized concurrently with the OCT interferogram and correlated with the known HF fingerprint to determine the wavenumber bias ($k_o$) of the swept source laser. Knowledge of wavenumber bias ($k_o$) allows accurate determination of the absolute wavenumber of each digitized sample throughout the spectral sweep, effectively removing any wavenumber offsets and/or phase instabilities in the laser source, wavemeter and sampling electronics. Knowledge of the magnitude of the fixed intervals and the optical frequency of at least one clock pulse provides knowledge of the optical frequency of every clock pulse provided by the optical clock.

The preceding exemplary phase sensitive OCT system is only one example of the contemplated systems for imaging tissues and nanoparticles. Variations in layout and equipment known to one skilled in the art are also contemplated.

Once the image of the plaque or macrophage is generated, the light source 114 is then selected to emit a pulsed laser light energy. In one embodiment of the invention, the pulsed light is in the green spectrum, approximately 532 nanometers for 0.01 to 2 seconds at a 10 Hz modulation frequency, which can cause a temperature increase of 18.6° C. It should be understood by those of ordinary skill in the art that different pulse durations can use for different sized nanoparticles in order to achieve sufficient thermal heating to obtain an enhanced thermal contrast of macrophages with an increased temperature. And by absorbing light energy, the nanoparticle temperature increases and produces thermal image taken by the thermal imaging apparatus.

Alternatively, the nanoparticles can be coated with a fluorescent material to detect the macrophages ingesting nanoparticles by fluoroscopy. Fluorescence would be triggered by optical energy reflecting by the laser generating element, and the frequencies involved would be tuned to pass through blood with out being absorbed by a wavelength of 1600 nm.

The thermal imaging apparatus 10 and method extends the concept of detecting infiltrating macrophages in vulnerable plaques (and other tissue of interest, such as retina) to therapeutic uses. Namely, the optical catheter or other device used to detect iron particles (magnetically oscillated and detected with phase sensitive OCT) can also be used to deliver therapeutic light. In one method, this could be through selective heating of the iron particles using a pulsed laser emission tuned to wavelength(s) preferentially absorbed by the iron particle. Because of the relative heat capacity differences of the iron and the surrounding tissue, and the very rapid heating/cooling, the cell containing the particle could be killed without inflicting damage to the surrounding cells or tissue. Since an objective is to reduce inflammation (caused by the macrophages), this is an important consideration—too much cell or tissue damage and necrosis would create additional inflammatory response.

Figure 5A:
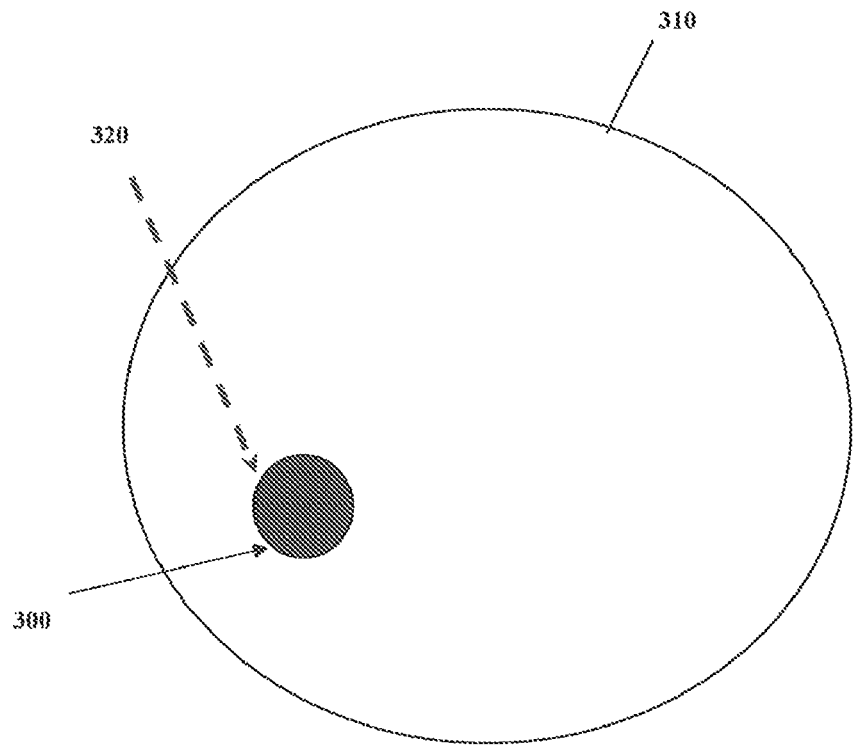
FIGS. 5A and 5B are a representative cell with a localized drug-containing nanoparticle and light or heat activated release of the drug
Figure 5B:
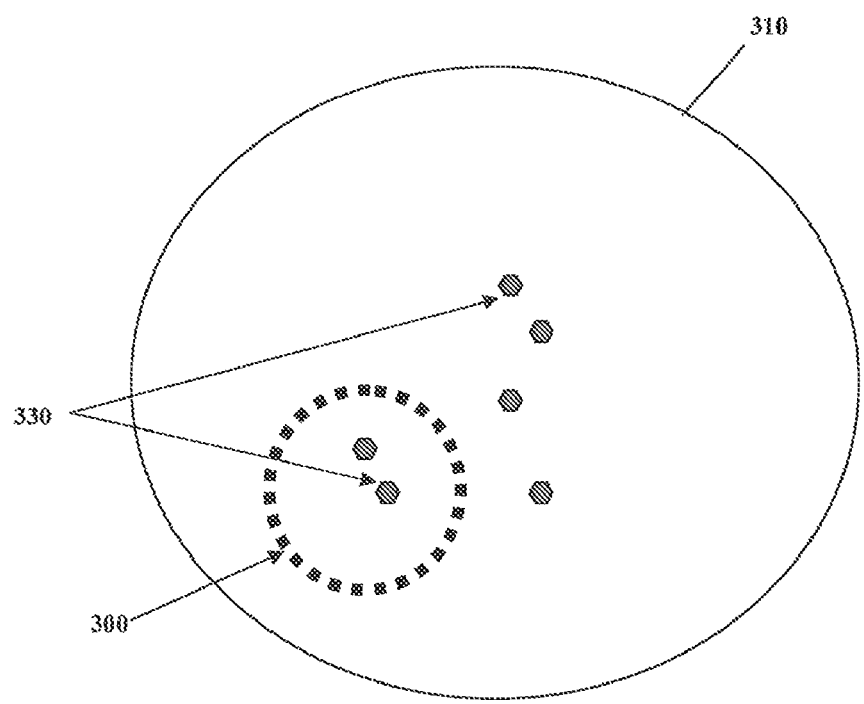
Figure 6A:
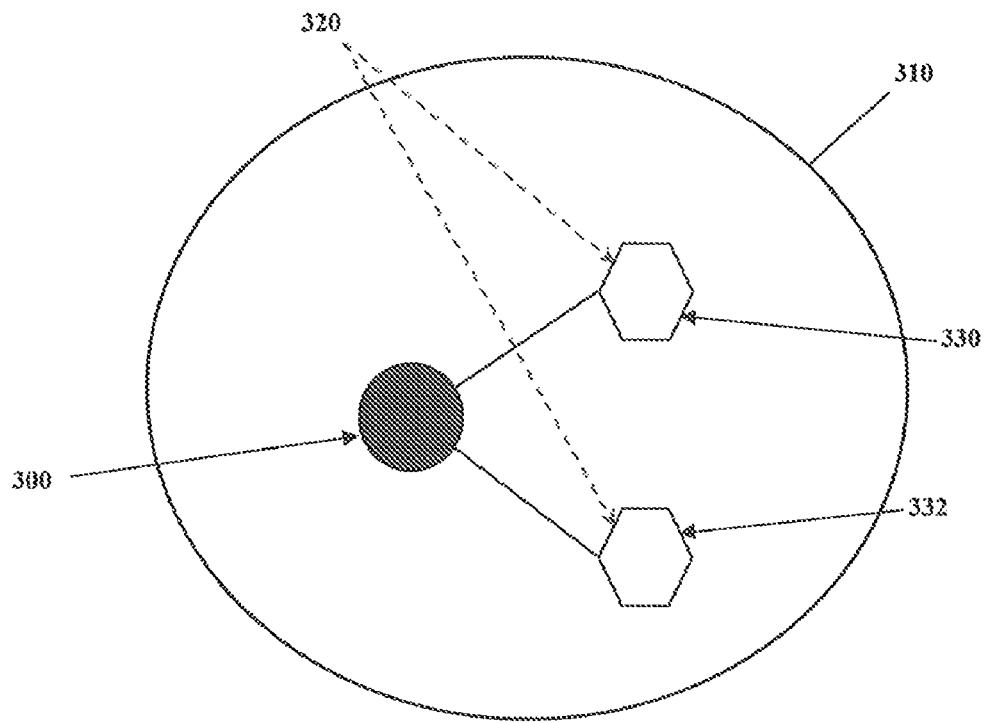
FIGS. 6A and 6B are a representative cell with a localized drug-containing nanoparticle with a light or heat-cleavable ligand.
Figure 6B:
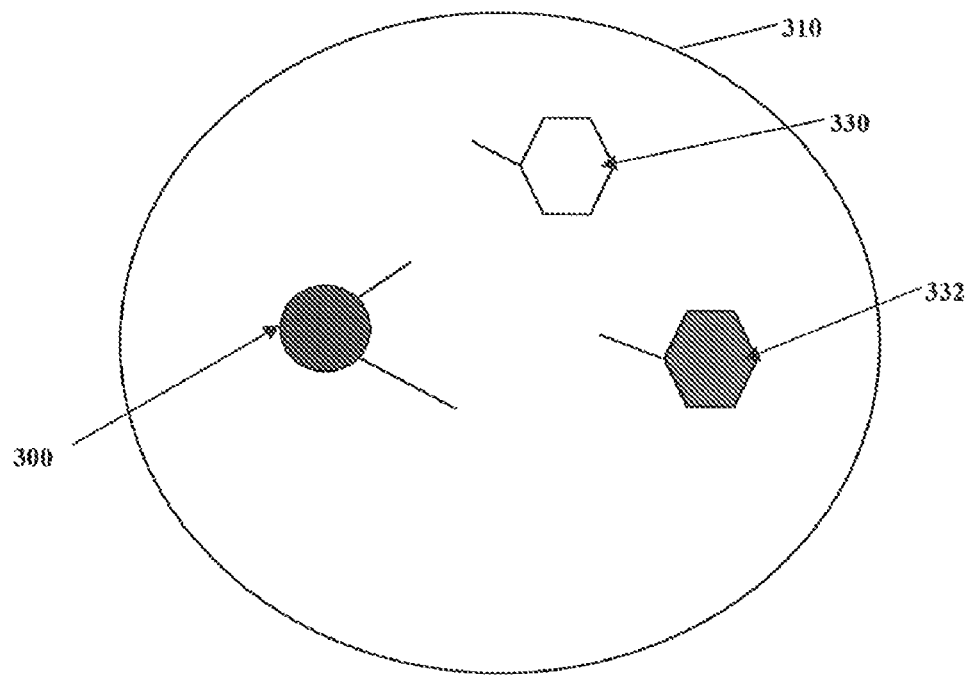

In FIGS. 5 and 6, the nanoparticle 300, or any nano- or micro-particle that is taken up with some selectivity by the target cell 310 or tissue type could be coated with light-responsive compounds such that the OCT or other incident light 320 would selectively release the light response compounds 330 to trigger cell death, neutralize the inflammatory response, or other cellular responses desirable to the control of the disease, depending on the nature of the photo-reactive compound(s) or systems employed. In one embodiment of the invention, the light responsive compounds could be a drug with a light-cleavable ligand 330 or a light-activated drug 332. The light responsive compounds 330 could also include, but not limited to, light activated or released pro-drugs, pharmacological agents, cleavable binding ligands conjugated to active or light activated compound, photo-reactive enzymes or toxins, immune system modulators, hormones, cytokines, antibodies, antibody fragments, peptides, DNA, RNA, mRNA, RNAi, other nucleic acid derivatives, or other molecules that are light activated and/or released, and interact with the cell replication or protein formation machinery, cell signaling pathways, protein activating or targeting or degrading pathways, apoptosis or necrosis mechanisms, antigen presentation or processing machinery, etc.

In addition, the action of the light activated/released compounds could be external to the targeted cell, either directly or though secondary effects or cascades, such that the desired activity is mediated by the surrounding tissue or cells, or cells recruited to the site.

The light used could be the same OCT light used to detect the cell, the pulsed laser light used to heat the particle, or some other wavelength chosen for its ability to interact in the desired fashion with the nanoparticle (or whatever can be substituted for "nanoparticle") or the compound(s) coating the nanoparticle.

Similarly, the compounds could be contained within the matrix of the particle, or within a hollow(s) in the particle, such that the incident light, or heating effect of the light, enables release and/or activation of the compound(s), either through chemical or mechanical effect, rupture, loss of structural integrity, phase separation, heat induced pressure changes or changes in pore size, or a change in adsorptive or absorptive nature of the matrix, or in the porosity or permeability of the matrix. The nanoparticle could be a single material, or a combination of materials that provide the required uptake, reactive, structural and chemical properties necessary to mediate the effects desired.

In this sense, the light activation properties could be mechanical in nature, that is, the changes in structure or chemistry of the particle, the release of particle material(s), or the breakdown of the particle material itself could provide the necessary effect. For example, fine particulate or fibrous materials derived from the particle upon contact with the light (sound or magnetism, or combination thereof) could be sufficient to elicit cell death, impede locomotion, cellular transport, microtubule assembly, mitosis, or provide other desired responses.

Exemplary multifunctional OCT nanoparticles (MONs) with an iron core for magnetic properties, a gold coating to tune wavelength absorption to 700 nm (above competing plaque components such as hemoglobin), and absorbed aminodextran coating for selective macrophage uptake.

If a magnetic field is used in the OCT nanoparticle system, then the magnetic field could be employed either alone or in combination with the light (OCT or other) to create the desired release and or activation of the compound(s) associated with the nanoparticle.

If ultrasound is used in the OCT nanoparticle system, then the ultrasound could be employed either alone or in combination with the light (OCT or other) to create the desired release and or activation of the compound(s) associated with the nanoparticle.

In another embodiment, an enhanced detection of cancer with ultrasound imaging is provided. Ultrasonography is the ultrasound-based diagnostic imaging technique used to visualize muscles and internal organs, their size, structures and any pathological lesions. "Ultrasound" applies to all acoustic energy with a frequency above human hearing (20,000 Hertz or 20 kilohertz). Typical diagnostic sonography scanners operate in the frequency range of 2 to 40 megahertz, hundreds of times greater than this limit. The choice of frequency is a trade-off between the image spatial resolution and penetration depth into the patient, with lower frequencies giving less resolution and greater imaging depth. Doppler ultrasonography uses the Doppler Effect to assess whether blood is moving towards or away from a probe, and its relative velocity. By calculating the frequency shift ($v_D$) of a particular sample volume, for example a jet of blood flow over a heart valve, its speed and direction can be determined and visualized. Ultrasonography and Doppler Ultrasonagraphy can best be understood by S. A. Kana *Introduction to physics in modern medicine*, Taylor & Francis, (2003). The basic physics of the Doppler effect involving acoustic and electromagnetic waves of OCT is similar and many of the signal processing techniques (hardware and software) used to estimate the Doppler shift of ultrasonic and optical coherence tomography signals is analogous.

Ultrasound imaging systems can be equipped with a 38 mm aperture, broadband (5-10 MHz) linear array transducer. Cells can be imaged in color power Doppler, power Doppler, M-mode and B-scan modes. B-scan sonogram images, also called the grayscale mode, are the typical ultrasound method to monitor or examine the human body using backscattering of acoustic waves. M-mode ultrasound employs a sequence of scans at a fixed ultrasound beam over a given time period. M-mode is used for visualizing rapidly moving subjects, such as heart valves. Compared to conventional B-scan images, Doppler ultrasound is used to assess changes in the frequency of reflected acoustic waves. Color power Doppler converts reflected acoustic waves that are Doppler shifted into colors that overlay the conventional B-scan images and can indicate the speed and direction of moving objects. Power Doppler ultrasound is most commonly used to evaluate moving objects and has higher sensitivity than the color power Doppler mode. The gain of the color power and Doppler imaging mode can be manually adjusted to suppress the background noise. If the settings of the ultrasound instrumentation remain unchanged, objective comparisons of each can be made.

Alternatively, the thermal imaging apparatus is operatively coupled to the OCT nanoparticle system and an Intravascular Ultrasound system. Such a system is generally described in U.S. Provisional Application Ser. No. 60/949,472.

EXAMPLES

The following examples are put forth so as to provide those of ordinary skill in the art with a complete disclosure and description of how the compositions, compositions, articles, devices, systems, and/or methods claimed herein are made and evaluated, and are intended to be purely exemplary and are not intended to limit the scope of compositions, compositions, articles, devices, systems, and/or methods. Efforts have been made to ensure accuracy with respect to numbers (e.g., amounts, temperature, etc.), but some errors and deviations should be accounted for.

Example 1

Thermal Wave Generation of Nanoparticles in an Elastic Medium

An expression for one-dimensional thermal wave signals in response to modulated laser irradiation in a test material is derived. The test material is composed of plain heat sources in a superficial layer, and background heat sources with a temperature increase that decays exponentially in depth (z) was assumed. Superparamagnetic iron oxide nanoparticles ("SPION") were regarded as plain heat sources in a superficial layer and homogeneous distribution of SPION was assumed. An insulating boundary condition (Q(heat flux)=−kdΔT/dz=0) at surface (z=0) in a semiinfinite half-space was assumed. Heat loss due to free convection at the airmaterial boundary was neglected. Thermal Green's function with insulating boundary condition ($G_{dT/dz=0}$) is $$G_{dT/dz=0} = G(z - z_{0,t}) + G(z + z_0, t) \quad (1.1)$$
$$= \frac{1}{2\sqrt{\pi Dt}} \exp\left(-\frac{(z - z_0)^2 + (z + z_0)^2}{4Dt}\right)$$

Here $z_o$ is depth of a superficial plane heat source, D is thermal diffusivity, and t is time. One-dimensional initial temperature distribution ($\Delta T(z, t)$) of a test material at a specific depth (z) and time (t) is written using the Green's function.

$$\Delta T(z, t) = \frac{1}{2\sqrt{\pi Dt}} \int_0^\infty \Delta T(z_0, t = 0) \exp\left(-\frac{(z - z_0)^2 + (z + z_0)^2}{4Dt}\right) dz_0 \quad (1.2)$$

Instantaneous PPTR signal ΔS(t) in response to laser irradiation is determined by integrating ΔT(z,t=0) along depth (z).

$$\Delta S(t) = C_d \mu_{a\_IR} \int_0^\infty \Delta T(z, t) \exp(-\mu_a z) \, dz_0 \quad (1.3)$$

where $\mu_{a\_IR}$ is an infrared absorption coefficient, $\mu_a$ is an absorption coefficient of a sample and $C_d$ is a normalized proportionality constant of an infrared camera.

Initial temperature distribution $\Delta T(z_o, t=0)$ in response to laser irradiation can be expressed by superposition of temperature increases due to two different kinds of heat sources: (1) nanometer-size point heat sources (SPION) uniformly distributed in a superficial layer; and (2) background heat sources in bulk of the test material.

A constant temperature ($\Delta T_{np}(z, t=0) = \Delta T_{np\_o}$) distribution was assumed for a superficial nanoparticle area and an exponentially decayed initial temperature distribution ($\Delta T_{BK}(z, t=0) = \Delta T_{BK\_o} \exp(-\mu_{a\_BK} z)$) was assumed for a background where $\mu_{a\_BK}$ is an absorption coefficient of a background (BK).

$\Delta T_{np\_o}$ can be expressed as a function of nanoparticle concentration $C_{np}$, number of particles/volume).

$$\Delta T_{np\_0} = \frac{\mu_{a\_np} \Phi}{\rho_{np} C_{p\_np}} = \frac{\sigma_{np} C_{np} \Phi}{\rho_{np} C_{p\_np}} \quad (1.4)$$

where $\mu_{a\_np}$ is an absorption coefficient, $\Phi$ is energy, $C_{p\_np}$ is heat capacity and $\rho_{np}$ is density of nanoparticles, respectively.

By completion of the integral in Equation 1.3 using a Green's function (Equation 1.1) for insulating boundary condition, $$\Delta S(t) = \frac{C_d \mu_{a\_IR}}{2} \int_0^\infty \Delta T(z, 0) \exp(\mu_a^2 Dt) \left\{ \begin{array}{c} \exp(\mu_a z) \mathrm{erfc}(u_+) \\ -\exp(-\mu_a z) \mathrm{erfc}(u_-) \end{array} \right\} dz \quad (1.5)$$

where $\mathrm{efrc}(\mu_\pm)$ is a complementary error function where $\mu_\pm$ is $\mu_{a\_IR}\sqrt{Dt} \pm z/2\sqrt{Dt}$ and $C_d$ is a proportionality constant determined by the infrared detection system Laplace transformation of $\Delta S(t)$ produces an analytical expression for the thermal wave thermal wave signal is, $$\Delta S_{np}(s) = \sqrt{\frac{D}{s}} \frac{C_d \mu_{a\_IR}}{(s + \mu_{a\_IR}\sqrt{Ds})} \frac{\sigma_{np} C_{np} \Phi}{\rho_{np} C_{p\_np}} \sinh\left(\sqrt{\frac{s}{D}} z^*\right) \quad (1.6)$$

where $z^*$ is the thickness of a nanoparticle (np) layer.

Thermal wave from the background (BK), $$\Delta S_{BK}(s) = \frac{C_d \mu_{a\_IR} \Delta T_{BK\_o}}{(s + \mu_{a\_IR}\sqrt{Ds})} \frac{\mu_{a\_BK}}{\mu_{a\_BK}^2 - s/D} \quad (1.7)$$

where $\mu_{a\_BK}$ is optical absorption coefficient of the background at the laser radiation wavelength. The total thermal wave signal is a sum of each contribution.

$\Delta S_{total}(s) = \Delta S_{SF}(s) + \Delta S_{BK}(s)$ $\|\Delta S_{total}(s)\|^2 = \|\Delta S_{SF}(s)\|^2 + \|\Delta S_{BK}(s)\|^2 + 2Re(\Delta S_{SF}(s) \cdot \Delta S_{BK}(s)^*)$ (1.8)

$\angle(\Delta S_{total}(s)) = \angle(\Delta S_{SF}(s) + \Delta S_{BK}(s))$ (1.9)

Example 2

Watanabe Heritable Hyperlipidemic (WHHL) Rabbit Artery

Twenty pulses of 532 nm laser light (Fluence rate=1.9-5.7 W/cm², power: 300-400 mW, pulse duration: 50 ms, spot diameter: 3-4.5 mm) irradiated Watanabe Heritable Hyperlipidemic ("WHHL") rabbit arteries (inner surface of artery wall) during 2 seconds with 10 Hz modulation frequency. Temperature change in response to laser irradiation was measured by an infrared focal plane array (IR-FPA) camera. The IR emission from the irradiated area (7-16 mm²) was imaged (Area: 1.5×1.5 cm²) with a spatial resolution of 60 µm per pixel. Calibration of IR emission was conducted to obtain temperature change assuming a unit emissivity of the rabbit arteries. Maximum temperature increase within the irradiated artery surface was measured. MION (2.96 cc)-injected WHHL rabbit arteries were compared with control WHHL rabbit arteries in terms of maximum temperature increase during 2-second modulated laser irradiation.

MION in macrophages of WHHL rabbit arteries were examined by thermal wave imaging. Thermal wave radiometric imaging used modulated laser irradiation. The modulation frequency ($f_m$) of 532 nm laser light was determined by computing a characteristic thermal-wave attenuation distance ($L_D$). A 10 Hz modulation frequency corresponded to $L_D$ (60 µm).

$$f_m = \frac{\chi}{\pi L_D^2} \quad (2)$$

where $f_m$ is laser modulation frequency, $\Omega$ is thermal diffusivity (0.11 mm²/s) of the tissue.

A large area visible photoreceiver (New Focus, Model 2032) detected modulated laser intensity. A sinusoidal signal in-phase with the detected laser intensity was generated using a low pass filter. The sinusoidal signal was Hilbert transformed and quadrature reference signals (real and imaginary) were generated. The reference signals were used to compute amplitude and phase for thermal wave imaging. An IR focal plane array (FPA) camera (Phoenix model, Indigo Systems, Santa Barbara, Calif.) recorded IR images (256×256 pixels, 1.5×1.5 cm², 60 µm/pixel) at 100 frames per second (FPS) from the irradiated rabbit artery. An individual image was low pass filtered by a 2-D convolution with a 3×3 pixels rectangular image block to increase a signal-to-noise ratio by removing a shot noise and repeated for all recorded image frames. The filtered sequential array of modulated IR emission intensity at each pixel was multiplied by the real or imaginary quadrature reference signals and averaged in time. Finally, the real and imaginary values of the processed IR emission at each pixel were obtained for thermal wave imaging. Magnitude and phase at each pixel were calculated and the thermal wave image was constructed.

Figure 7A:
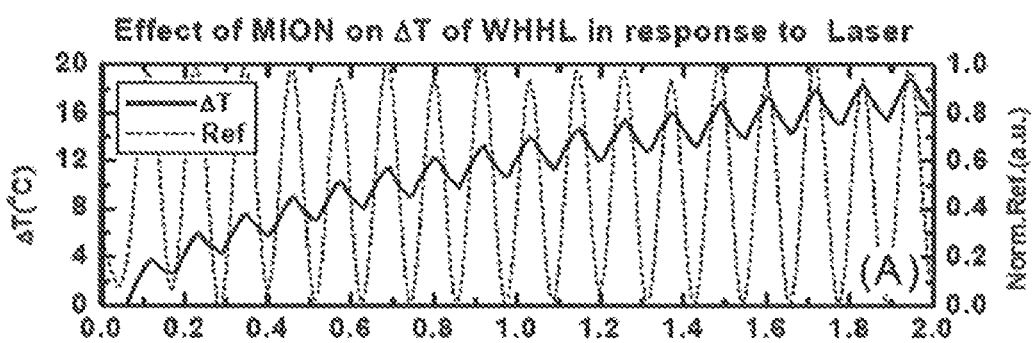
FIGS. 7A and 7B are graphs representing the temperature increase of metallic nanoparticles in a rabbit artery as determined by the thermal wave imaging apparatus.
Figure 7B:
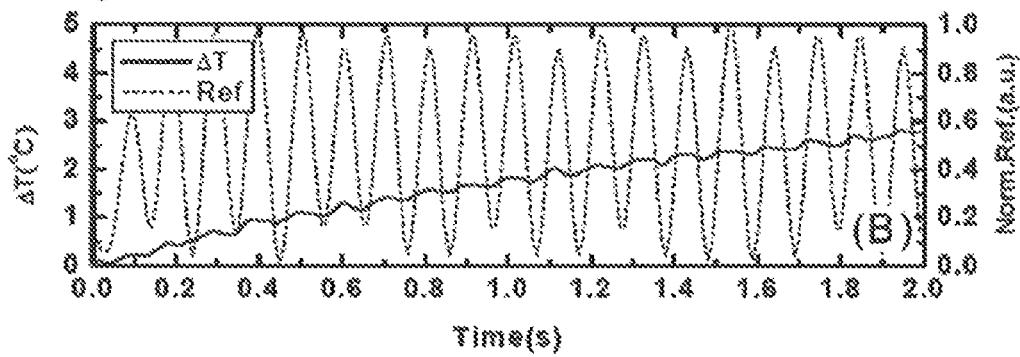

Temperature increase of WHHL rabbit arteries were measured from both a MION-injected and control rabbit. MION-injected rabbit arteries showed higher temperature increase than that in control rabbit arteries. As shown in FIGS. 7A and 7B, the temperature increase (19° C.) of a MION-injected rabbit artery in response to 2-second pulsed laser irradiation (Repetition rate=10 Hz) was much higher than the temperature increase (3° C.) of a control rabbit artery. The nanoparticles can be heated to a tune of 18.6° C. hotter than nonmetallic nanoparticles, as shown in FIGS. 7A and 7B. FIG.

7A shows temperature increase of a WHHL rabbit with intravenously injected MION. FIG. 7B shows the temperature increase of a control WHHL rabbit. The dotted line shows normalized reference signal of modulated laser irradiation. Pulsed light in the green spectrum for 2 seconds at a 10 Hz modulation frequency and a power of 400 mW heated MION nanoparticles by sufficiently above the 0.3° C., which inflammatory plaques exhibit. In one embodiment of the invention, the fluence rate=141.5 W/cm$^2$, power: 400 mW, pulse duration: 100 ms, spot diameter=600 µm. IR emission from laser-heated iron oxide nanoparticle solutions was converted to temperature increase assuming a unit emissivity. Temperature increase of each nanoparticle solution was normalized by nanoparticle concentration MION in macrophages of WHHL, rabbit arteries were examined by thermal wave imaging. Thermal wave radiometric imaging used modulated laser irradiation. The modulation frequency ($f_m$) of 532 nm laser light was determined by computing a characteristic thermal-wave attenuation distance ($L_D$). A 10 Hz modulation frequency corresponded to $L_D$ (60 µm).

Maximum temperature increase of MION-injected WHHL rabbit arteries and control WHHL rabbit artery were measured by calibrating IR intensity to temperature within irradiated area. The average of maximum temperatures of MION and control rabbits (n=9) was calculated. The average maximum temperature increase of MION-injected rabbit arteries was 5.99±5.4° C. while that of control rabbit arteries was 4.18±1.29° C. The higher temperature increase may be due to additional heating due to absorption of laser energy by MION. The amount of MION within the irradiated area is dependent on the number of macrophages in each artery.

Figure 8A:
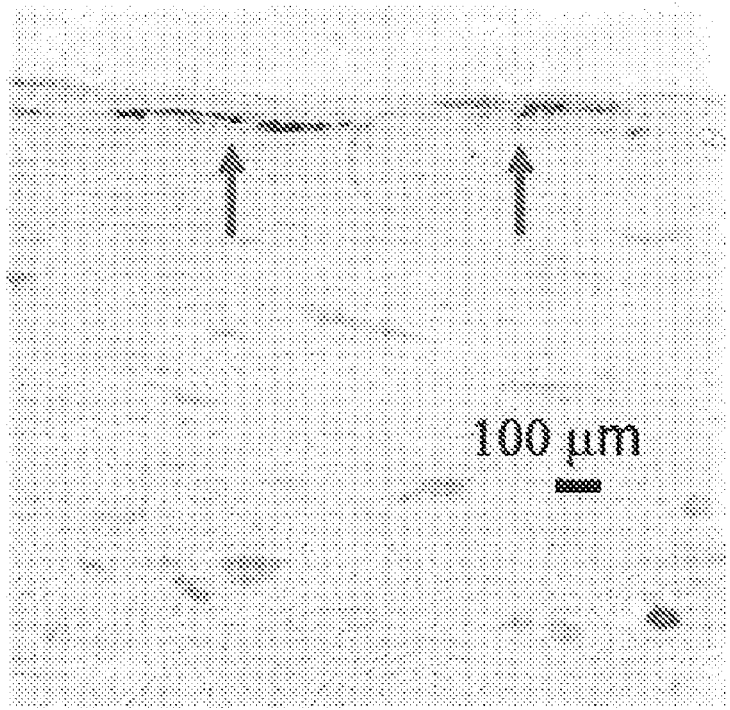
FIGS. 8A and 8B are histological sections of macrophages stained with RAM 11 and Prussian Blue in WHHL rabbit arteries, respectively.
Figure 8B:
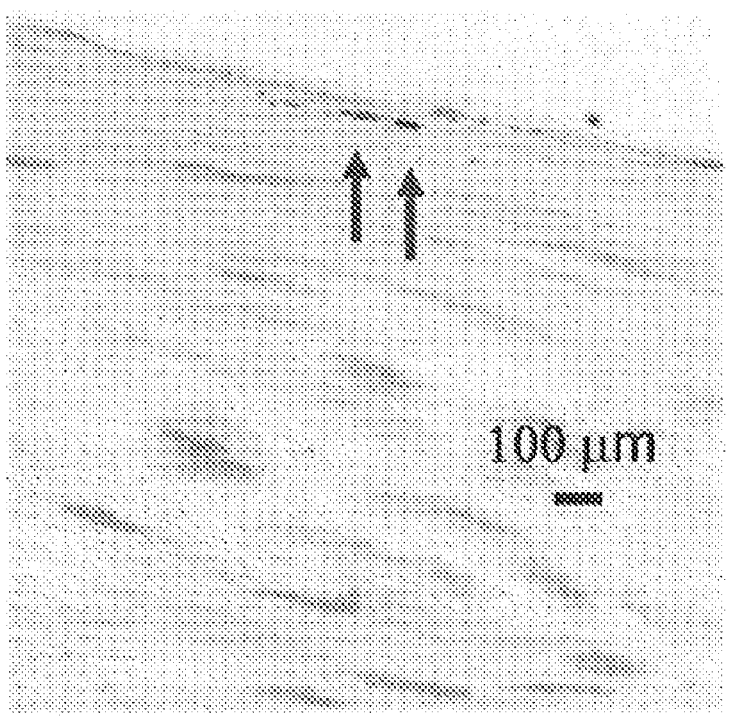

The temperature heterogeneity in plaques is related to vulnerable plaques which have high density of macrophages. Macrophages may have absorption at 532 nm wavelength and caused the temperature increase for control WHHL rabbit arteries, as shown in FIGS. 8A and 8B. FIGS. 8A and 8B are macrophages stained with Rabbit macrophage antibody ("RAM 11") and Prussian Blue in WHHL rabbit arteries, respectively. Hemoglobin and residual hemoglobin staining of artery wall can contribute to the background signal due to strong absorption of hemoglobin in 400 to 600 nm. Ideal wavelength of pulsed laser irradiation is near infrared (NIR) wavelengths (800-1300 nm) to avoid competing chromophores such as water and hemoglobin.

Example 3

Thermal Wave Radiometric Imaging: Comparison of Experiments and Theory

Analytical solutions for magnitude and phase of a thermal wave were derived (Equations 1.8 and 1.9). Measured thermal wave is a sum of thermal waves from nanoparticles and background absorbers. The effect of nanoparticle concentration on magnitude and phase of a total thermal wave was investigated by the derived analytical solutions. In analytical solutions, the surface temperature increase of a nanoparticle layer was varied in comparison to that of background absorbers. The ratio (=ΔTo-np/ΔTo-BK) between nanoparticle and background surface temperature increase was varied from 0.01 to 0.15 (0.01, 0.05, 0.1 and 0.15). At a specific modulation frequency of pulsed laser irradiation, as surface temperature of a nanoparticle layer increases, magnitude of a total thermal wave increases, however, phase decreases.

Figure 9A:
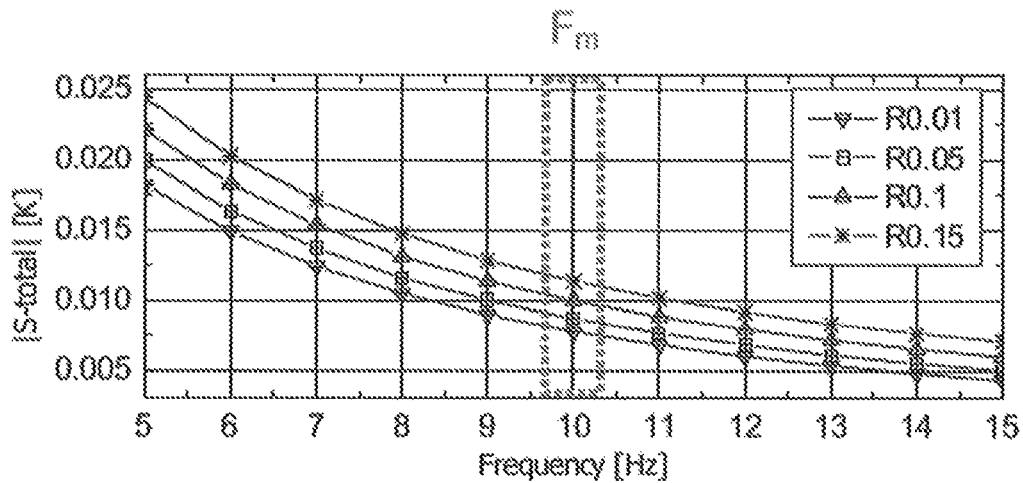
FIGS. 9A and 9B are graphs of the magnitude and phase ('Ang') of thermal wave ($\Delta S(s)$): $\mu_a\_Bk=18$ [1/mm], $\mu_a\_IR=50$ [1/mm], $\Delta To\text{-}np=0.01, 0.05, 0.1,$ and $0.15$ [° C.], $\Delta To\text{-}Bk=1$ [° C.], where the legends show ratios ($\Delta To\text{-}np/\Delta To\text{-}BK$) between initial temperature increase of superficial nanoparticles area ($\Delta To\text{-}np$) and background ($\Delta To\text{-}BK$).
Figure 9B:
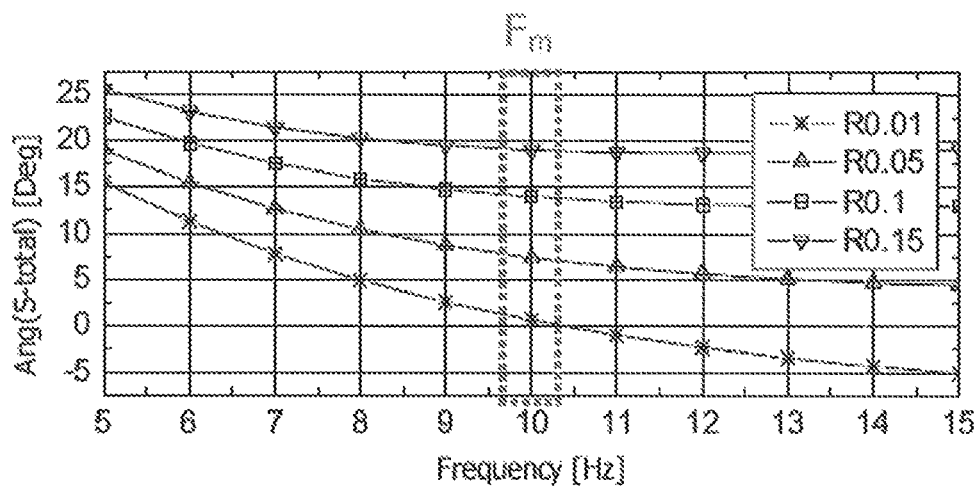

Phase of the thermal wave image was more sensitive to change in nanoparticle concentration than magnitude, as shown in FIGS. 9A and 9B, and decreased quickly as concentration of nanoparticles (ΔTo-np) increased. The dark dots in thermal wave phase image for a MION-injected rabbit artery can be explained by a lower phase with higher nanoparticle concentration. FIGS. 9A and 9B are magnitude and phase ('Ang') of thermal wave (ΔS(s)): $\mu_a\_Bk$=18 [1/mm], $\mu_a\_IR$=50 [1/mm], ΔTo-np=0.01, 0.05, 0.1, and 0.15 [° C.], ΔTo-Bk=1 [° C.]. Legends show ratios (ΔTo-np/ΔTo-BK) between initial temperature increase of superficial nanoparticles area (ΔTo-np) and background (ΔTo-BK).

Careful selection of a laser modulation frequency must be completed to observe both magnitude and phase difference between nanoparticle and background areas. A 10 Hz modulation frequency was selected to target nanoparticles at 60 µm depth (Equation 2) in the rabbit artery. In this theoretical analysis, magnitude and phase at 10 Hz in analytical solutions, as shown in FIGS. 9A and 9B, looked feasible to screen nanoparticles for thermal wave imaging. The initial surface temperature increase ratio (ΔTo-np/ΔTo-BK) based on measured temperature increase, as shown in FIGS. 7A and 7B of MION-injected and control WHHL rabbit arteries was from 0.33 to 2. Therefore, 10 Hz modulation frequency of 532 nm pulsed laser irradiation is sufficient to detect MION from the background area of a rabbit artery for both magnitude and phase. An approximate upper limit of concentration of MION was calculated by measured temperature increase of MION-injected and control rabbit arteries. The upper limit of MION concentration was $4.54 \times 10^{12}$.

Figure 10:
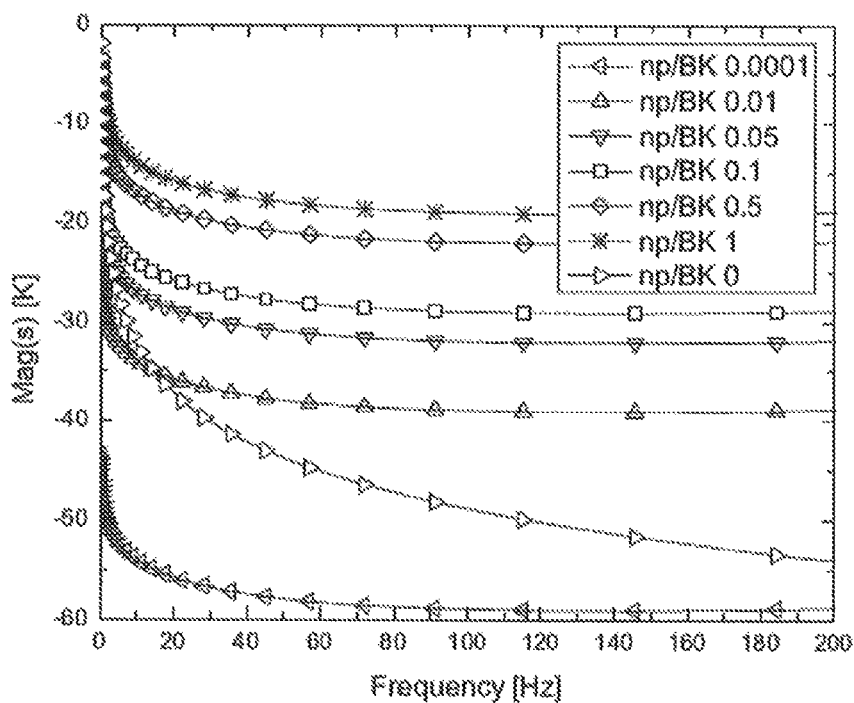
FIG. 10 is a graph of the magnitudes of thermal waves (dS-np(s) and dS-bk (s)): $\mu_a\_BK=1$ [1/mm], $\mu_a\_IR=100$ [1/mm], $\Delta To\text{-}np=0.0001\text{--}1$ [° C.], $\Delta To\text{-}BK=1$ [° C.], where the legends for nanoparticles ("np") show ratios ($\Delta To\text{-}np/\Delta To\text{-}BK$) between initial temperature increase of superficial nanoparticles area ($\Delta To\text{-}np$) and background ($\Delta To\text{-}BK$).
Figure 11:
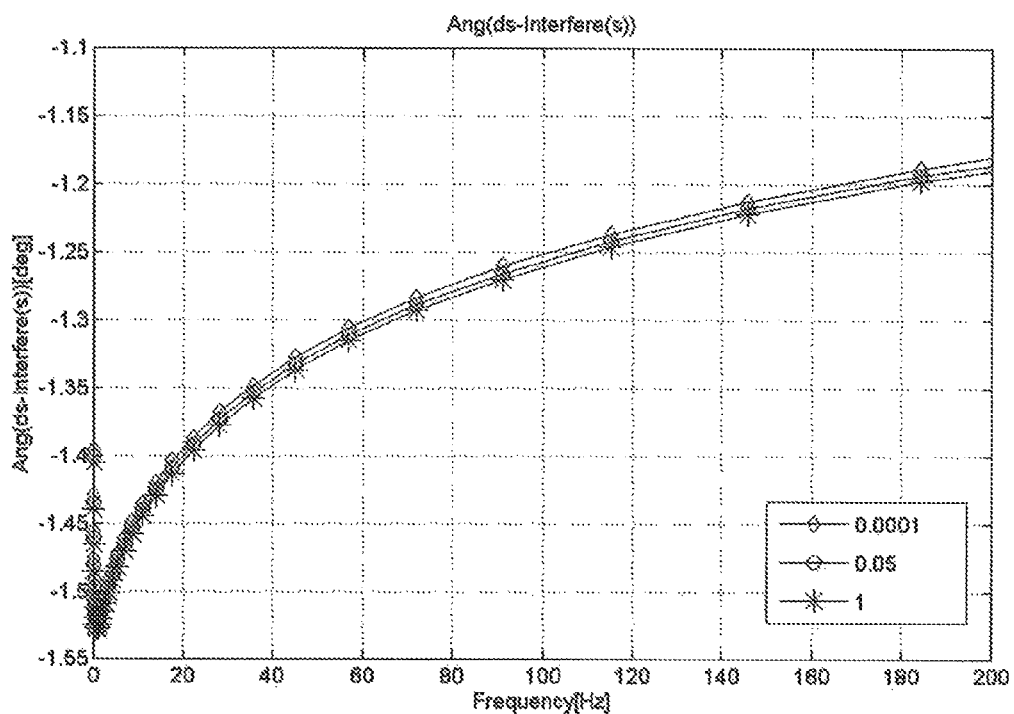
FIG. 11 is a graph of the phase of interference term of thermal wave. Legends for nanoparticles (np) show ratios (dFo-np/dTo-BK) between initial temperature increase of superficial nanoparticles area (dTo-np) and background (dTo-BK).

The magnitude and phase of thermal waves from nanoparticles embedded in a WHHL, rabbit artery and background absorbers were simulated and comparable. The modulation frequency dependence of thermal wave magnitude and phase also was investigated, as shown in FIGS. 10 and 11. FIG. 10 is a graph of the magnitudes of thermal waves (dS-np(s) and dS-bk (s)): $\mu_a\_BK$=1 [1/mm], $\mu_a\_IR$=100 [1/mm], ΔTo-np=0.0001–1 [° C.], ΔTo-BK=1 [° C.]. Legends for nanoparticles ("np") show ratios (ΔTo-np/ΔTo-BK) between initial temperature increase of superficial nanoparticles area (ΔTo-np) and background (ΔTo-BK). BK represents background. Magnitude of thermal waves from both discrete nanoparticles and background absorbers decrease as modulation frequency increases. However magnitude of thermal wave from background absorbers decreases much faster than that from discrete nanoparticles. Since the nanoparticle thermal wave magnitude reached minimum magnitude after initial fast decrease and increases as modulation frequency increases, contribution of background absorbers to total thermal wave magnitude becomes weaker at higher modulation frequencies.

Thermal wave magnitude due to nanoparticles embedded in a rabbit artery was assumed to be very small compared to that generated from background absorbers. In simulation, background absorbers were assumed to be distributed homogeneously in a semi-infinite layer. Nanoparticles were homogeneously distributed in a thin (60 µm) layer. Therefore, the ratio with regard to thermal wave magnitude, or initial temperature increase, between nanoparticles and background absorbers is less than 1.

The phase change of thermal wave interference term in Equation 1.8 with different modulation frequency was shown in FIG. 11. FIG. 11 is a graph of the phase of interference term of thermal wave. Legends for nanoparticles (np) show ratios (dTo-np/dTo-BK) between initial temperature increase of superficial nanoparticles area (dTo-np) and background (dTo-BK). BK represents background.

Figure 12:
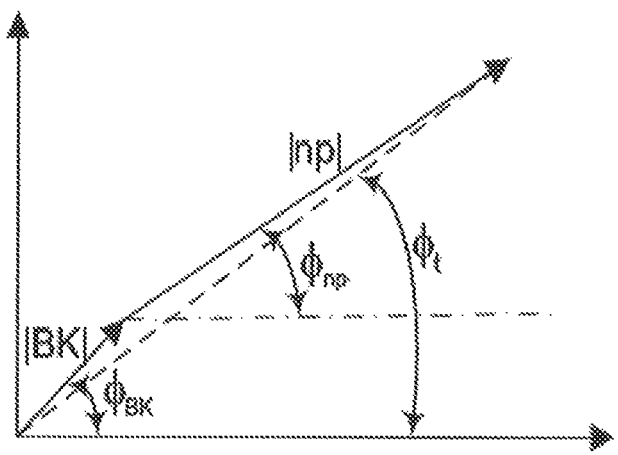
FIG. 12 is a graph of the phase ($\Phi t$) of total thermal wave in complex number plain vector domain, where $|np|$ and $\Phi_{np}$: magnitude and phase of thermal wave from nanoparitcles, and $|BK|$ and $\Phi BK$ are the magnitude and phase of thermal wave from background absorbers.

The interference term of the total thermal wave indicates phase difference between two thermal waves from nanoparticles and background absorbers. FIG. 12 showed phase of the total thermal wave. FIG. 12 shows a graph of the phase (Φt) of total thermal wave in complex number plain vector domain, where |np| and $\Phi_{np}$ are the magnitude and phase of thermal wave from nanoparitcles, and |BK| and ΦBK are the magnitude and phase of thermal wave from background absorbers.

It seemed nanoparticle presence in background absorbers of the rabbit artery does not affect phase change pattern but it does decrease phase values at a specific modulation frequency as nanoparticle thermal wave strength (dTo-np) increased.

Although the interference phase difference is small (<0.01 degree), the phase difference in thermal wave imaging was amplified by multiplication by the modulated laser intensity. Theoretically, if a thermal wave is exactly in-phase with the modulated laser intensity, the phase is lower than the phase of a thermal wave which is out of-phase with the modulated laser intensity.

Figure 13:
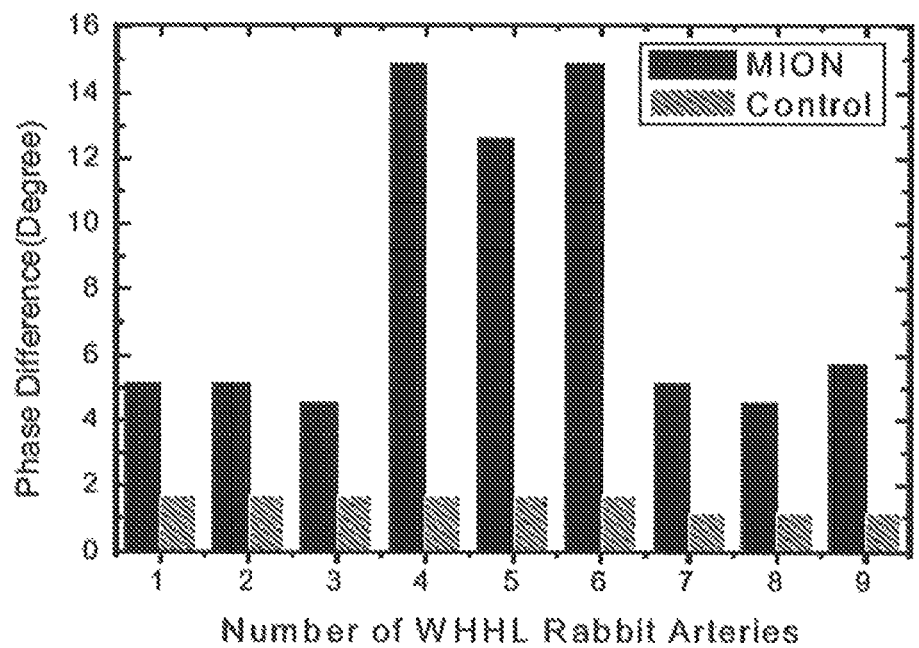
FIG. 13 is a graph of the phase difference between MION embedded region and background, where the control: artery of rabbit which was injected by saline solution, and MION is the artery of rabbit which was injected by MION.

In a thermal wave phase image of a MION-injected WHHL, rabbit, a pixel index of discrete dark dots was selected and phase grayscale value was obtained by converting to a 8-bit intensity. Phase from a background region within a heated area was also collected and phase difference was calculated. This procedure was repeated three times per each image and five images for control rabbits and five images for MION rabbits were chosen for phase difference measurements. The phase difference between a nanoparticle embedded region and a background was measured and shown in FIG. 13. FIG. 13 is a graph of the phase difference between MION embedded region and background, where the control is the artery of rabbit which was injected by saline solution, and MION is the artery of rabbit which was injected by MION.

The MION-injected rabbits showed greater phase difference (p=0.0014) than control rabbits probably due to MION presence. In detail, phase difference of MION-injected rabbit (n=9) was 8.08±4.46 [Degree] while phase difference of control rabbits (n=9) was 1.53±0.28 [Degree]. The phase difference was related to surface temperature increase. Higher temperature increase of a MION-injected rabbit artery than control rabbit artery also indicated MION presence within radiated area.

Selection of nanoparticles which have absorption in "water window" wavelengths (Near IR: 800-1300 nm) may be required to avoid a competing chromophore such as hemoglobin, water, or protein. Alternatively, the blood vessels may be flushed with saline, as generally known in the medical arts, where saline flushes the blood vessel of blood. The absorption of gold nanoshells shifts optical resonance from visible to near IR. Therefore, pulsed NIR laser irradiation, such as 1064 nm, of gold nano-shell may improve the detection of atherosclerotic plaque by using thermal wave imaging. However, selection of optimal nanoparticles and laser wavelengths can enhance detection of macrophage.

All patent and non-patent literature cited herein is hereby incorporated by references as if listed in its entirety herein for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of imaging a vulnerable plaque comprising:
    a. administering a plurality of metallic nanoparticles to a subject that have been selected to have an absorption avoiding hemoglobin;
    b. heating at least one administered nanoparticle, wherein the heating includes a modulation frequency selected at one or more frequencies to observe a magnitude and a phase difference of thermal waves between the nanoparticles and the background areas of the nanoparticles; and
    c. imaging the heated metallic nanoparticles with a thermal sensor.

2. The method of claim 1, further comprising localizing at least one administered nanoparticle within a macrophage located within the subject.

3. The method of claim 2, wherein the macrophage is localized in an atherosclerotic plaque in the subject.

4. The method of claim 1, further comprising configuring at least one nanoparticle to localize to a target site in the subject.

5. The method of claim 1, wherein the nanoparticles are substantially spherical and have a diameter from about 0.1 nanometers to about 1000.0 nanometers in size.

6. The method of claim 1, wherein the heating step further comprises inactivating a macrophage located within the plaque.

7. The method of claim 6, wherein the heating step further comprises reflecting the light energy off a mirror element, and rotating the mirror element in a 360 degree arc.

8. The method of claim 6, wherein the heating step further comprises generating light energy emitted by a pulsed laser source.

9. The method of claim 1, wherein the thermal wave from the background areas (BK) is given by the formula:

$$\Delta S_{BK}(s) = \frac{C_d \mu_{a\_IR} \Delta T_{BK\_o}}{(s + \mu_{a\_IR}\sqrt{Ds})} \frac{\mu_{a\_BK}}{\mu_{a\_BK}^2 - s/D},$$

where $\mu_{a\_BK}$ is the optical absorption coefficient of the background at a laser radiation wavelength, $\mu_{a\_IR}$ is an infrared absostion coefficien is an absorption coefficient of a sample, D is thermal diffusivity, $\Delta T_{BK\_o}$ is the exponentially decayed initial temperature distribution for the background, s is the thermal wave, and $C_d$ is a normalized proportionality constant of an infrared camera.

10. The method of claim 1, wherein the thermal sensor is a part of an optical coherence tomography imaging system.

11. The method of claim 10, wherein the optical coherence tomography system is phase sensitive.

12. The method of claim 1, further comprising imaging the heated metallic nanoparticles with an ultrasound imaging system.

13. The method of claim 1, wherein the nanoparticle is coated with a light-responsive compound that is selectively released upon incident light.

14. The method of claim 1, wherein the nanoparticles are multifunctional nanoparticles including an aminodextran coating.

15. The method of claim 1, wherein the heating includes a wavelength of light between at least 800-1300 nm to avoid chromophores in the background of the nanoparticles.

16. The method of claim 1, wherein the modulation frequency is between at least 10 and 200 Hz.

17. The method of claim 1, wherein the heating of the at least one administered nanoparticle is normalized by the selection of nanoparticle concentration.

18. A method of imaging a vulnerable plaque comprising:
a. administering a plurality of metallic nanoparticles to a subject;
b. heating at least one administered nanoparticle, wherein the heating includes a modulation frequency selected at one or more frequencies to observe a magnitude and a phase difference of thermal waves between the nanoparticles and the background areas of the nanoparticles, wherein the thermal wave from the background areas (BK) is given by the formula:

$$\Delta S_{BK}(s) = \frac{C_d \mu_{a\_IR} \Delta T_{BK\_o}}{\left(s + \mu_{a\_IR}\sqrt{Ds}\right)} \frac{\mu_{a\_BK}}{\mu_{a\_BK}^2 - s/D},$$

where $\mu_{a\_BK}$ is the optical absorption coefficient of the background at a laser radiation wavelength, $\mu_{a\_IR}$, is an infrared absorption coefficient, $\mu_a$ is an absorption coefficient of a sample, D is thermal diffusivity, $\Delta T_{BK\_o}$ is the initial temperature distribution for the background, s is the thermal wave, and $C_d$ is a proportionality constant of the thermal sensor; and
c. imaging the heated metallic nanoparticles with a thermal sensor, wherein the thermal sensor is a part of a phase-sensitive optical coherence tomography system.

19. The method of claim 18, wherein the nanoparticle is coated with a light-responsive compound that is selectively released upon incident light.

20. The method of claim 18, wherein the nanoparticles are multifunctional nanoparticles including an aminodextran coating.

* * * * *